United States Patent
Boghossian et al.

(10) Patent No.: US 9,902,799 B2
(45) Date of Patent: Feb. 27, 2018

(54) URETHANE-MODIFIED PREPOLYMERS CONTAINING PENDENT ALKYL GROUPS, COMPOSITIONS AND USES THEREOF

(71) Applicant: PRC-DeSoto International, Inc., Sylmar, CA (US)

(72) Inventors: Razmik Boghossian, Sylmar, CA (US); Ahmed Sharaby, Canyon County, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 52 days.

(21) Appl. No.: 14/937,904

(22) Filed: Nov. 11, 2015

(65) Prior Publication Data

US 2017/0129986 A1 May 11, 2017

(51) Int. Cl.
- *C08G 18/12* (2006.01)
- *C07C 321/14* (2006.01)
- *C08G 18/76* (2006.01)
- *C08G 18/38* (2006.01)
- *C08G 18/65* (2006.01)
- *C09K 3/10* (2006.01)

(52) U.S. Cl.
CPC ............ *C08G 18/12* (2013.01); *C07C 321/14* (2013.01); *C08G 18/3868* (2013.01); *C08G 18/3876* (2013.01); *C08G 18/65* (2013.01); *C08G 18/7671* (2013.01); *C09K 3/1021* (2013.01)

(58) Field of Classification Search
CPC . C08G 18/3876; C08G 18/12; C08G 18/3868
See application file for complete search history.

(56) References Cited

U.S. PATENT DOCUMENTS

| | | |
|---|---|---|
| 2,466,963 A | 4/1949 | Ferguson et al. |
| 3,615,972 A | 10/1971 | Morehouse, Jr. et al. |
| 3,864,181 A | 2/1975 | Wolinski et al. |
| 3,881,047 A | 4/1975 | Massy et al. |
| 3,975,194 A | 8/1976 | Famand et al. |
| 4,006,273 A | 2/1977 | Wolinski et al. |
| 4,044,176 A | 8/1977 | Wolinski et al. |
| 4,366,307 A | 12/1982 | Singh et al. |
| 4,582,756 A | 4/1986 | Niiuma et al. |
| 4,609,762 A | 9/1986 | Morris et al. |
| 4,623,711 A | 11/1986 | Morris et al. |
| 4,722,943 A | 2/1988 | Melber et al. |
| 4,787,451 A | 11/1988 | Mitchell |
| 5,225,472 A | 7/1993 | Cameron et al. |
| 5,270,364 A | 12/1993 | Schwartz et al. |
| 5,284,888 A | 2/1994 | Morgan |
| 5,525,262 A | 6/1996 | Castellucci et al. |
| 5,536,756 A | 7/1996 | Kida et al. |
| 5,663,219 A | 9/1997 | Chokshi et al. |
| 5,912,319 A | 6/1999 | Zook et al. |
| 5,942,556 A | 8/1999 | Friedlander et al. |
| 5,955,143 A | 9/1999 | Wheatley et al. |
| 6,172,179 B1 | 1/2001 | Zook et al. |
| 6,235,800 B1 | 5/2001 | Kyuno et al. |
| 6,403,752 B1 | 6/2002 | House et al. |
| 6,486,297 B2 | 11/2002 | Zook et al. |
| 6,509,418 B1 | 1/2003 | Zook et al. |
| 6,525,168 B2 | 2/2003 | Zook et al. |
| 6,613,436 B2 | 9/2003 | Ambrose et al. |
| 6,875,800 B2 | 4/2005 | Vanier et al. |
| 6,894,086 B2 | 5/2005 | Munro et al. |
| 6,998,107 B2 | 2/2006 | Unger |
| 7,009,032 B2 | 3/2006 | Bojkova et al. |
| 7,097,883 B2 | 8/2006 | Sawant et al. |
| 7,879,955 B2 | 2/2011 | Rao et al. |
| 8,513,339 B1 | 8/2013 | Keledjian et al. |
| 2004/0097643 A1 | 5/2004 | Bons |
| 2004/0247792 A1 | 12/2004 | Sawant et al. |
| 2005/0010003 A1 | 1/2005 | Sawant et al. |
| 2005/0287348 A1 | 12/2005 | Faler et al. |
| 2006/0252881 A1 | 11/2006 | Zhang et al. |
| 2006/0270796 A1 | 11/2006 | Ichikawa et al. |
| 2007/0299217 A1 | 12/2007 | Sawant et al. |

(Continued)

FOREIGN PATENT DOCUMENTS

RU   2003117463 A   12/2004
RU      2263699 C2    5/2005

(Continued)

OTHER PUBLICATIONS

Thioplast G4 Product Data Sheet. Jan. 2009. https://www.akzonobel.com/sulfurderivatives/system/images/AkzoNobel_Thioplast_G4_tcm95-69009.pdf.*

Wikipedia, The Free Encyclopedia, "Polyphenylene sulfide", page last modified on Oct. 1, 2015, retrieved from https://en.wikipedia.org/wiki/Poly(p-phenylene_sulfide)#cite_ref-Parker_1-0 on Nov. 11, 2015, 3 pages.

*Primary Examiner* — Michael L Leonard
(74) *Attorney, Agent, or Firm* — William R. Lambert

(57) ABSTRACT

Adducts and prepolymers comprising pendent alkyl groups are disclosed. Polythiol adducts prepared by reacting a polythiol with a ketone and urethane-extended polythiol adducts. The polythiol adducts can be terminated with isocyanate groups. Compositions comprising the isocyanate-terminated polythiol adducts, isocyanate-terminated sulfur-containing prepolymers, and diisocyanates can be combined with polyamine or polyepoxide curing agents to provide curable compositions. Cured compositions are suitable for aerospace coating and sealant applications. The compositions can also include a low specific gravity filler and, when cured, meet the requirements of aerospace sealant applications.

36 Claims, No Drawings

(56) References Cited

U.S. PATENT DOCUMENTS

| | | |
|---|---|---|
| 2010/0010133 A1 | 1/2010 | Zook et al. |
| 2010/0041839 A1 | 2/2010 | Anderson et al. |
| 2010/0286307 A1 | 11/2010 | Anderson |
| 2011/0319559 A1 | 12/2011 | Kania et al. |
| 2012/0234205 A1 | 9/2012 | Hobbs et al. |
| 2012/0238707 A1 | 9/2012 | Hobbs et al. |
| 2013/0079485 A1 | 3/2013 | Cai et al. |
| 2013/0082214 A1 | 4/2013 | Sharaby et al. |
| 2013/0344340 A1* | 12/2013 | Senkfor ............ C08G 18/10 428/419 |
| 2013/0345371 A1 | 12/2013 | Anderson et al. |

FOREIGN PATENT DOCUMENTS

| | | |
|---|---|---|
| WO | 2000/075221 | 12/2000 |
| WO | 2001/007154 A1 | 2/2001 |
| WO | 2001/066622 A | 9/2001 |
| WO | 2001/066642 A1 | 9/2001 |
| WO | 2006/060272 A2 | 6/2006 |
| WO | 2007/063001 A | 6/2007 |
| WO | 2008/040508 A | 4/2008 |
| WO | 2009/095739 A1 | 8/2009 |

\* cited by examiner

URETHANE-MODIFIED PREPOLYMERS CONTAINING PENDENT ALKYL GROUPS, COMPOSITIONS AND USES THEREOF

FIELD

The invention relates to polythiol adducts prepared by reacting a polythiol with a ketone and urethane-extended polythiol adducts. The polythiol adducts can be terminated with isocyanate groups. Compositions comprising the isocyanate-terminated polythiol adducts, isocyanate-terminated sulfur-containing prepolymers, and diisocyanates can be combined with polyamine or polyepoxide curing agents to provide curable compositions. Cured compositions are suitable for aerospace coating and sealant applications. The compositions can also include a low specific gravity filler and, when cured, meet the requirements of aerospace sealant applications.

BACKGROUND

Coatings and sealants used in the aerospace industry must meet demanding performance requirements. The coatings and sealants must exhibit excellent initial adhesion, tensile strength and elongation and must maintain acceptably high values following exposure to aviation fluids, high temperature, and/or salt spray. In addition, to reduce the weight of aerospace vehicles it is also desirable that aerospace coatings and sealants exhibit a low specific gravity.

Aerospace compositions having a low specific gravity can include a high loading of low density filler. The addition of a high volume or weight percent of a low density filler can increase the viscosity of the uncured composition to an extent that the ability to apply the composition and/or the useful working time of the composition is not acceptable. To provide homogeneous properties, it is also important that a filler be uniformly dispersed throughout the coating or sealant.

Low density aerospace coatings and sealants having homogenously dispersed fillers, improved adhesion, and enhanced flexibility are desired.

SUMMARY

Isocyanate-terminated urethane-containing prepolymers of the present invention can be combined with a polyamine curing agent and a low density filler to provide low density coatings and sealants that meet the requirements of aerospace sealant applications. The isocyanate-terminated urethane-containing prepolymers can be prepared by reacting a diisocyanate, a polythiol adduct, and a thiol-terminated sulfur-containing prepolymer.

According to the present invention, polythiol adducts can comprise the condensation reaction products of reactants comprising a polythiol and a ketone.

According to the present invention, polythiol adducts can have the structure of Formula (6):

$$HS-(-R^1-S-R^2-S-)_n-R^1-SH \quad (6)$$

wherein,
n is an integer from 1 to 10;
each $R^1$ independently comprises a moiety of Formula (1a):

$$-[-(CHR^3)_p-X-]_q-(CHR^3)_r- \quad (1a)$$

wherein,
each $R^3$ comprises hydrogen or methyl;
each X is independently selected from O and S;
p is an integer from 2 to 6;
q is an integer from 1 to 5; and
r is an integer from 2 to 10; and
each $R^2$ independently is a moiety having the structure of Formula (3a):

$$-C(-R^4)_2- \quad (3a)$$

wherein each $R^4$ independently comprises $C_{1-5}$ alkyl.

According to the present invention, urethane-extended polythiol adducts can comprise the reaction product of reactants comprising: a polythiol adduct provided by the present disclosure; and a diisocyanate.

According to the present invention, urethane-extended polythiol adducts can have the structure of Formula (7):

$$HS-[-A-S-C(=O)-NH-R^5-NH-C(=O)-S-]_m-A-SH \quad (7)$$

wherein,
each $R^5$ independently comprises a core of a diisocyanate;
m is an integer from 1 to 10;
each A independently comprises a moiety having the structure of Formula (6a):

$$-(-R^1-S-R^2-S-)_n-R^1- \quad (6a)$$

wherein,
n is an integer from 1 to 10;
each $R^1$ independently comprises a structure of Formula (1a):

$$-[-(CHR^3)_p-X-]_q-(CHR^3)_r- \quad (1a)$$

wherein,
each $R^3$ comprises hydrogen or methyl;
each X is independently selected from O and S;
p is an integer from 2 to 6;
q is an integer from 1 to 5; and
r is an integer from 2 to 10; and
each $R^2$ independently comprises a moiety having the structure of Formula (3a):

$$-C(-R^4)_2- \quad (3a)$$

wherein each $R^4$ independently comprises $C_{1-5}$ alkyl.

According to the present invention, isocyanate-terminated urethane-containing prepolymers can comprise the reaction product of reactants comprising: the polythiol adduct provided by the present disclosure; a thiol-terminated sulfur-containing prepolymer; and a diisocyanate.

According to the present invention, isocyanate-terminated urethane-containing prepolymers can comprise the reaction products of reactants comprising: an isocyanate-terminated sulfur-containing prepolymer, a polythiol adduct, and a diisocyanate; wherein, the isocyanate-terminated prepolymer comprises the reaction product of reactants comprising a diisocyanate and a thiol-terminated sulfur-containing prepolymer; and the polythiol adduct comprises the polythiol adduct provided by the present disclosure.

According to the present invention, isocyanate-terminated urethane-containing prepolymers can comprise an isocyanate-terminated urethane-containing prepolymer of Formula (15a), an isocyanate-terminated urethane-containing prepolymer of Formula (15b), or a combination thereof:

$$D-S-P-S-D \quad (15a)$$

$$\{D-S-P-S-V'-\}_zB \quad (15b)$$

wherein,
each D independently comprises a moiety having the structure of Formula (16a), Formula (16b), Formula (16c), Formula (16d), Formula (16e), Formula (16f), Formula (16g), or a combination of any of the foregoing:

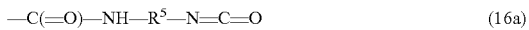  (16a)

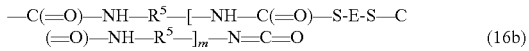  (16b)

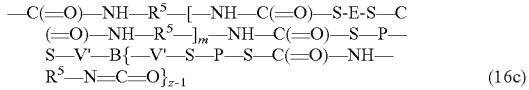  (16c)

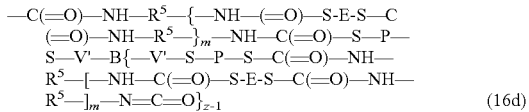  (16d)

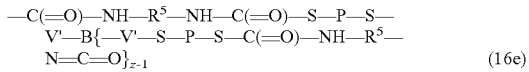  (16e)

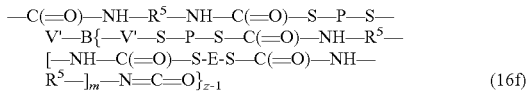  (16f)

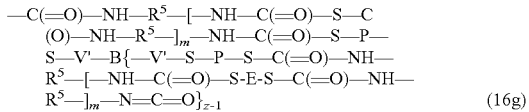  (16g)

wherein,
each $R^5$ independently comprises a core of a diisocyanate;
each m is an integer from 1 to 10;
each E comprises a core of a polythiol adduct;
each P comprises a polythioether moiety or a polysulfide moiety;
B represents a core of a z-valent, polyfunctionalizing agent $B(-V)_z$ wherein,
z is an integer from 3 to 6; and
each V is a moiety comprising a terminal group reactive with a thiol; and
each —V'— is derived from the reaction of —V with a thiol.

According to the present invention, isocyanate-terminated urethane-containing prepolymers can comprise an isocyanate-terminated urethane-containing prepolymer of Formula (19):

  (19)

wherein,
G is a moiety of Formula (9d):

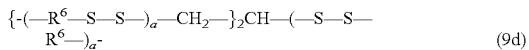  (9d)

wherein,
each a is independently an integer from 1 to 50;
the sum of each a is an integer from 5 to 60; and
each $R^6$ comprises a moiety having the structure $-(CH_2)_2-O-CH_2-O-(CH_2)_2-$;
and
each D independently comprises a moiety having the structure of Formula (20a), Formula (20b), Formula (20c) or Formula (20d):

  (20a)

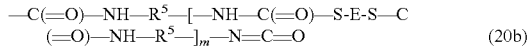  (20b)

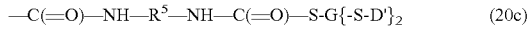  (20c)

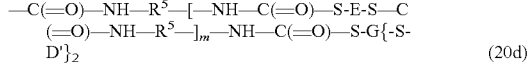  (20d)

wherein,
each $R^5$ independently comprises a core of a diisocyanate; and
each m is an integer from 1 to 10;
each E comprises a core of a polythiol adduct or a core of a urethane-containing polythiol adduct; and
each D' comprises a moiety of Formula (20a) or a moiety of Formula (20b).

According to the present invention, compositions can comprise an isocyanate-terminated urethane-containing prepolymer provided by the present disclosure.

According to the present invention, parts can comprise a sealant prepared from a composition of composition provided by the present disclosure.

According to the present invention, methods of sealing a part can comprise: providing a curable composition comprising the composition provided by the present disclosure; applying the curable composition to at least a portion of a surface of a part; and curing the applied curable composition to seal the part.

Reference is now made to certain compounds, compositions, sealants, and methods of the present invention. The disclosed compounds, compositions, sealants, and methods are not intended to be limiting of the claims. To the contrary, the claims are intended to cover all alternatives, modifications, and equivalents.

DETAILED DESCRIPTION

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10.

Also, in this application, the use of "or" means "and/or" unless specifically stated otherwise, even though "and/or" may be explicitly used in certain instances.

A dash ("-") that is not between two letters or symbols is used to indicate a point of bonding for a substituent or between two atoms. For example, —CONH$_2$ is bonded to another chemical moiety through the carbon atom.

"Alkyl" refers to a mono-radical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. An alkyl group can be $C_{2-6}$ alkyl, $C_{2-4}$ alkyl, or, $C_{2-3}$ alkyl. Examples of alkyl groups include methyl, ethyl, n-propyl, iso-propyl, n-butyl, iso-butyl, tert-butyl, n-hexyl, n-decyl, tetradecyl, and the like. An alkyl group is $C_{2-6}$ alkyl, $C_{2-4}$ alkyl, or $C_{2-3}$ alkyl. It will be appreciated that a branched alkyl has at least three carbon atoms.

"Alkanediyl" refers to a diradical of a saturated, branched or straight-chain, acyclic hydrocarbon group, having, for example, from 1 to 18 carbon atoms ($C_{1-18}$), from 1-14 carbon atoms ($C_{1-14}$), from 1-6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. The alkanediyl can be $C_{2-14}$ alkanediyl, $C_{2-10}$ alkanediyl, $C_{2-8}$ alkanediyl, $C_{2-6}$ alkanediyl, $C_{2-4}$ alkanediyl, or $C_{2-3}$ alkanediyl. Examples of alkanediyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, decane-1,10-diyl, dodecane-1,12-diyl, and the like. It will be appreciated that a branched alkanediyl has at least three carbon atoms.

"Cycloalkanediyl" refers to a diradical saturated monocyclic or polycyclic hydrocarbon group. The cycloalkanediyl group can be $C_{3-12}$ cycloalkanediyl, $C_{3-8}$ cycloalkanediyl, $C_{3-6}$ cycloalkanediyl, or $C_{5-6}$ cycloalkanediyl. Examples of cycloalkanediyl groups include cyclohexane-1,4-diyl, cyclohexane-1,3-diyl, and cyclohexane-1,2-diyl.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. The cycloalkyl and/or cycloalkanediyl group(s) is $C_{3-6}$, $C_{5-6}$, and, cyclohexyl or cyclohexanediyl. The alkyl and/or alkanediyl group(s) is $C_{1-6}$, $C_{1-4}$, $C_{1-3}$, or methyl, methanediyl, ethyl, or ethane-1,2-diyl. The alkanecycloalkane group is $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, or $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. The alkanecycloalkanediyl group is $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, or $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Heterocycloalkanediyl" refers to a cycloalkanediyl group in which one or more of the carbon atoms are replaced with a heteroatom, such as N, O, S, or P. In certain embodiments of heterocycloalkanediyl, the heteroatom is selected from N and O.

"Core of a diisocyanate" refers to the moiety between the two diisocyanate groups of a diisocyanate. For example, for a diisocyanate having the general structure O═C═N—R—N═C═O, the moiety —R— represents the core of the diisocyanate between the two isocyanate groups —N═C═O. As a further example, the core of the diisocyanate 4,4'-methylene dicyclohexyl diisocyanate (H$_{12}$MDI) having the structure:

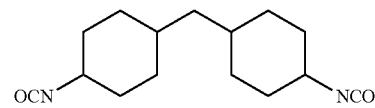

is represented by the structure

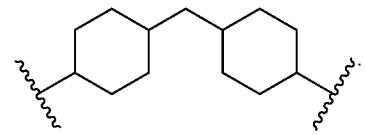 [SMILES: *C1CCC(CC2CCC(*)CC2)CC1]

A "curable composition" refers to a composition that comprises at least two reactants capable of reacting to form a cured composition. For example, a curable composition can comprise a thiol-terminated polythioether prepolymer and a polyepoxide capable of reacting to form a cured polymer network. A curable composition may include a catalyst for the curing reaction and other components such as, for example, fillers, pigments, and adhesion promoters. The selection of the other components can be made as appropriate for a particular use such as formulated for sealant applications or formulated for coating applications. A curable composition may be curable at ambient conditions such as room temperature and humidity, or may require exposure to elevated temperature, moisture, or other condition(s) to initiate and/or accelerate the curing reaction. A curable composition may initially be provided as a two part composition including a base component and an accelerator component. The base composition can contain one of the reactants participating in the curing reaction such as a thiol-terminated polythioether prepolymer and the accelerator composition can contain the other reactant such as a polyepoxide. The two compositions can be mixed shortly before use to provide a curable composition. A curable composition can exhibit a viscosity suitable for a particular method of application. For example, a Class A sealant composition, which is suitable for brush-on applications can be characterized by a viscosity from 150 Poise to 500 Poise. A Class B sealant composition, which is suitable for fillet seal applications can be characterized by a viscosity from 8,000 Poise to 16,000 Poise. A Class C sealant composition, which is suitable for fay seal applications can be characterized by a viscosity from 1,000 Poise to 4,000 Poise. After the two compositions are combined and mixed, the curing reaction can proceed and the viscosity of the curable composition can increase and at some point will no longer be workable. The period of time between when the two compositions are mixed to form the curable composition and when the curable composition can no longer be reasonably applied to a surface for its intended purpose is referred to as the working time. As can be appreciated, the working time can depend on a number of factors including, for example, the curing chemistry, the application method, and the temperature. The working time can also be referred to as the pot life. Once a curable composition is applied to a surface (and during application), the curing reaction proceeds to provide a cured composition. A cured composition develops a tack-free surfaces and fully cures over a period of time. This time period can be referred to as the curing time. A curable composition can be considered to be cured when the surface is tack-free, or can be considered to be cured when the Shore A hardness of the surface is 35 A.

As used herein, "polymer" refers to oligomers, homopolymers, and copolymers. Unless stated otherwise, molecular weights are number average molecular weights for polymeric materials indicated as "Mn" as determined, for example, by gel permeation chromatography using a polystyrene standard in an art-recognized manner. A polymer includes a prepolymer. A prepolymer such as a thiol-terminated polythioether prepolymer provided by the present disclosure can be combined with a curing agent to provide a curable composition, which can cure to provide a cured polymer network.

"Derived from the reaction of —V with a thiol" refers to a moiety —V'— that results from the reaction of a thiol group with a moiety comprising a terminal group reactive with a thiol group. For example, a group V— can comprise $CH_2=CH-CH_2-O-$, where the terminal alkenyl group $CH_2=CH-$ is reactive with a thiol group —SH. Upon reaction with a thiol group, the moiety —V'— is —$CH_2$—$CH_2$—$CH_2$—O—.

A "backbone of a polythioether prepolymer" refers to a polythioether prepolymer between the terminal reactive groups. For example, a backbone of a polythioether prepolymer having the structure:

$$HS-R^1-[-S-(CH_2)_2-O-[-R^2-O-]_m-(CH_2)_2-S-R^1-S-]_n-H$$

can have the structure:

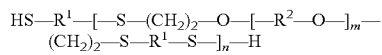
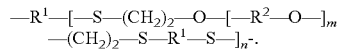

A "polythioether moiety or a polysulfide moiety" refers to a moiety comprising multiple thioether —S— groups or disulfide groups —S—S—, respectively. A polythioether moiety can comprise the backbone of a polythioether prepolymer. A polysulfide moiety can comprise the backbone of a polythioether prepolymer.

A "core of a polythiol adduct or a core of a urethane-containing polythiol adduct" refers to the segment of the polythiol adduct between the reactive terminal groups. For example, the core of a urethane-containing polythiol adduct of Formula (6);

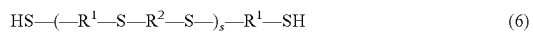

has the structure of Formula (6a):

where s, $R^1$ and $R^2$ are defined herein. A core of a compound can also be referred to as a backbone such as a backbone of an adduct or a backbone of a prepolymer.

A "polythiol adduct" comprises un-extended polythiol adducts and urethane-extended polythiol adducts. A un-extended polythiol adduct does not contain urethane segments within the adduct backbone and a urethane-extended polythiol adduct contains urethane segments within the adduct backbone. A polythiol adduct provided by the present disclosure can comprise pendent alkyl groups in the adduct backbone.

A "urethane-containing polythiol adduct," also referred to as a urethane-extended polythiol adduct can comprise one or more urethane segments within the backbone of the polythiol adduct.

Compositions

Compositions according to the invention can comprise an isocyanate-terminated urethane-containing prepolymer. The isocyanate-terminated urethane-containing prepolymer can comprise pendent alkyl groups in the polymer backbone. The pendent alkyl groups can interfere with a hydrogen bonding between polymer chains of the composition, thereby improving the flexibility of the cured composition. For example, the pendent alkyl groups can reduce the amount of hydrogen bonding between urethane and ester linkages between separate polymer chains, or even within a polymer chain. Pendent alkyl groups can also lower the free energy of the composition thereby improving the spread of the composition onto a substrate surface and the adhesion of the coating or sealant to the substrate. Pendent alkyl groups can also increase the flexibility of a cured coating or sealant by reducing the hard segment domain content of the cured polymer. Pendent alkyl groups can be incorporated into an isocyanate-terminated urethane-containing prepolymer using precursors such as polythiol adducts comprising pendent alkyl groups.

Isocyanate Prepolymer

An isocyanate-terminated urethane-containing prepolymer can comprise the reaction product of reactants comprising a polythiol adduct, a thiol-terminated sulfur-containing prepolymer, and a diisocyanate.

Isocyanate-terminated urethane-containing prepolymers provided by the present disclosure can also be prepared by first reacting a thiol-terminated sulfur-containing prepolymer or a combination of thiol-terminated sulfur-containing prepolymers with a diisocyanate or a combination of diisocyanates to provide an isocyanate-terminated sulfur-containing prepolymer; followed by reaction of the isocyanate-terminated sulfur-containing prepolymer with a polythiol adduct and a diisocyanate.

Polythiol Adducts

Un-Extended Polythiol Adducts

Polythiol adducts provided by the present disclosure can comprise un-extended polythiol adducts, urethane-extended polythiol adducts, or combinations thereof. An un-extended polythiol adduct does not contain urethane groups in the backbone. A urethane-extended polythiol adduct comprises urethane groups in the backbone of the adduct.

A polythiol adduct can comprise a dithiol adduct, a trithiol adduct, a urethane-extended dithiol adduct, a urethane-extended trithiol adduct, or a combination of any of the foregoing. Polythiol adducts can have a thiol functionality, for example, from 2 to 6, from 2 to 5, or from 2 to 4.

A polythiol adduct can comprise the reaction product of reactants comprising a polythiol and a ketone. A polythiol adduct can comprise pendent alkyl groups extending from the backbone of the adduct.

Examples of suitable polythiols for preparing a polythiol adduct include dithiols having the structure of Formula (1):

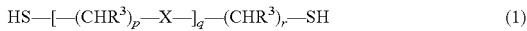

$$HS-[-(CHR^3)_p-X-]_q-(CHR^3)_r-SH \qquad (1)$$

wherein,
each $R^3$ comprises hydrogen or methyl;
each X is independently selected from O and S;
p is an integer from 2 to 6;
q is an integer from 1 to 5; and
r is an integer from 2 to 10.

In dithiols of Formula (1), each $R^3$ can be hydrogen, X can be S, and dithiols have the structure of Formula (2a), or each $R^3$ can be hydrogen, X can be O, and dithiols have the structure of Formula (2b):

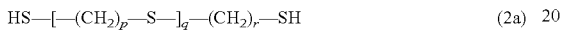
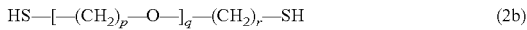

$$HS-[-(CH_2)_p-S-]_q-(CH_2)_r-SH \qquad (2a)$$

$$HS-[-(CH_2)_p-O-]_q-(CH_2)_r-SH \qquad (2b)$$

In dithiols of Formula (1), Formula (2a), and Formula (2b), each $R^3$ can be hydrogen.

In dithiols of Formula (1), Formula (2a), and Formula (2b), at least one $R^3$ can be methyl.

In dithiols of Formula (1), Formula (2a), and Formula (2b), p can be 2, 3, 4, 5, or 6.

In dithiols of Formula (1), Formula (2a), and Formula (2b), q can be 1, 2, 3, 4, or 5.

In dithiols of Formula (1), Formula (2a), and Formula (2b), r can be 2, 3, 4, 5, 6, 7, 8, 9, or 10.

In dithiols of Formula (1), Formula (2a), and Formula (2b), each $R^3$ can be hydrogen, p can be 2, q can be 2, and r can be 2.

In dithiols of Formula (1), Formula (2a), and Formula (2b), p can be 2, q can be 2, and r can be 2.

A polythiol can comprise a dithiol of Formula (2a), a dithiol of Formula (2b), or a combination thereof. A dithiol can comprise dimercaptodiethylsulfide (DMDS), 3,6-dioxa-1,8-octanedithiol (DMDO), or a combination thereof.

Ketones

Examples of suitable ketones for preparing a polythiol adduct include low molecular weight ketones such as, propan-2-one, methyl ethyl ketone (butan-2-one), pentan-2-one, hexan-2-one, pentan-3-one, 3-methylbutan-2-one, 3-methylpentan-2-one, 4-methylhexan-3-one, 2-methylpentan-3-one, and 2,4-dimethylpentan-3-one. A ketone can comprise methyl ethyl ketone. Higher molecular weight ketones may also be used.

Suitable ketones can have the structure of Formula (3):

$$R^4-(=O)-R^4 \qquad (3)$$

where each $R^4$ independently comprises $C_{1-5}$ alkyl.

In ketones of Formula (3), each $R^4$ can independently comprise methyl, ethyl, n-propyl, n-butyl, n-pentyl, isopropyl, sec-butyl, pentan-2-yl, 2-methylbutyl, isopentyl, 3-metylbutan-2-yl, or isobutyl.

In ketones of Formula (3), each $R^4$ can independently comprise methyl or ethyl. In ketones of Formula (3), one $R^4$ can be methyl and the other $R^4$ can be ethyl, both $R^4$ can be methyl, or both $R^4$ can be ethyl.

A polythiol adduct can comprise the reaction product of a polythiol and a ketone such as the reaction product of a polythiol of Formula (1), Formula (2a), Formula (2b), or a combination of any of the foregoing; and a ketone of Formula (3).

Polythiol adducts can comprise dithiol adducts having the structure of Formula (4):

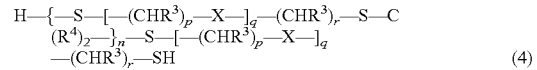

$$H-\{-S-[-(CHR^3)_p-X-]_q-(CHR^3)_r-S-C(R^4)_2-\}_n-S-[-(CHR^3)_p-X-]_q-(CHR^3)_r-SH \qquad (4)$$

where X, p, q, r, $R^3$ and $R^4$ are defined as in Formula (1) and Formula (3), and n can be an integer from 1 to 10. For example, in polythiol adducts of Formula (4), n can be an integer from 1 to 4, an integer from 1 to 3, 1, 2, 3, 4, 5, 6, 7, 8, 9, or 10.

In polythiol adducts of Formula (4), X can be S and a polythiol adduct can have the structure of Formula (4a), X can be O and a polythiol adduct can have the structure of Formula (4b), or can be a combination thereof:

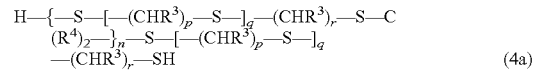

$$H-\{-S-[-(CHR^3)_p-S-]_q-(CHR^3)_r-S-C(R^4)_2-\}_n-S-[-(CHR^3)_p-S-]_q-(CHR^3)_r-SH \qquad (4a)$$

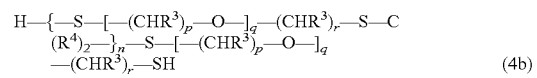

$$H-\{-S-[-(CHR^3)_p-O-]_q-(CHR^3)_r-S-C(R^4)_2-\}_n-S-[-(CHR^3)_p-O-]_q-(CHR^3)_r-SH \qquad (4b)$$

where p, q, r, $R^3$ and $R^4$ are defined as in Formula (1) and Formula (3), and n can be an integer from 1 to 10.

In polythiol adducts of Formula (4), Formula (4a), and Formula (4b), p can be 2, q can be 2, r can be 2, each $R^4$ can independently comprise methyl or ethyl, and each $R^3$ can be hydrogen.

When each $R^3$ in polythiol adducts of Formula (4), Formula (4a), or Formula (4b), is hydrogen, a polythiol adduct can have the structure of Formula (5), Formula (5a), or Formula (5b), respectively:

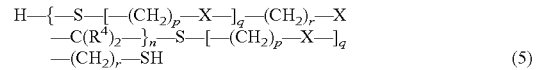

$$H-\{-S-[-(CH_2)_p-X-]_q-(CH_2)_r-X-C(R^4)_2-\}_n-S-[-(CH_2)_p-X-]_q-(CH_2)_r-SH \qquad (5)$$

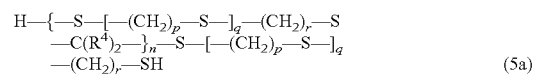

$$H-\{-S-[-(CH_2)_p-S-]_q-(CH_2)_r-S-C(R^4)_2-\}_n-S-[-(CH_2)_p-S-]_q-(CH_2)_r-SH \qquad (5a)$$

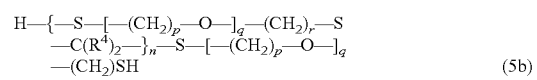

$$H-\{-S-[-(CH_2)_p-O-]_q-(CH_2)_r-S-C(R^4)_2-\}_n-S-[-(CH_2)_p-O-]_q-(CH_2)SH \qquad (5b)$$

where X, p, q, r, n, and $R^4$ are defined as in Formula (1), Formula (3), and Formula (4).

In polythiol adducts of Formula (5), Formula (5a), and Formula (5b), p can be 2, q can be 2, r can be 2, and each $R^4$ can independently comprise methyl or ethyl.

A polythiol adduct can have the structure of Formula (6):

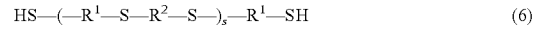

$$HS-(-R^1-S-R^2-S-)_s-R^1-SH \qquad (6)$$

wherein,
s is an integer from 1 to 10;
each $R^1$ independently comprises a moiety of Formula (1a):

$$-[-(CHR^3)_p-X-]_q-(CHR^3)_r- \qquad (1a)$$

wherein,
each $R^3$ is selected from hydrogen and methyl;
each X is independently selected from O and S;
p is an integer from 2 to 6;
q is an integer from 1 to 5; and
r is an integer from 2 to 10;

each $R^2$ independently comprises a moiety having the structure of Formula (3a):

$$—C(—R^4)_2— \qquad (3a)$$

wherein each $R^4$ independently comprises $C_{1-5}$ alkyl.

In polythiol adducts of Formula (6), s can be from 1 to 6, from 1 to 5, from 1 to 4, from 1 to 3, from 1 to 2, or from 2 to 6. In polythiol adducts of Formula (6), s can be 1, 2, 3, 4, 5, 6, 7, 8, 9, or 10.

In polythiol adducts of Formula (6), each $R^3$ can be hydrogen, q can be 1, 2, or 3, r can be 2 or 3, and p can be 2 or 3.

Polythiol adducts can comprise the reaction product of a condensation reaction between a polythiol and a ketone. Polythiol adducts can comprise the reaction product of reactants comprising DMDS and/or DMDO, and methyl ethyl ketone. The reaction can be catalyzed by an appropriate catalyst such as para-toluene sulfonic acid. The mole ratio of polythiol to ketone can be selected to provide a desired number of pendent alkyl groups along the polythiol adduct backbone and/or to provide polythiol adducts having a desired molecular weight.

Polythiol adducts provided by the present disclosure can be characterized by a molecular weight, for example, from 250 Daltons to 1,000 Daltons, from 300 Daltons to 800 Daltons, or from 350 Daltons to 600 Daltons and can be liquid or solid at room temperature.

Urethane-Extended Polythiol Adducts

Polythiol adducts provided by the present disclosure can comprise urethane-extended polythiol adducts. Urethane-extended polythiol adducts comprise urethane groups in the backbone of the adduct.

Urethane-extended polythiol adducts can comprise the reaction products of a polythiol adduct and a diisocyanate. Examples of suitable polythiol adducts for preparing urethane-extended polythiol adducts include those having the structure of Formula (4), Formula (4a), Formula (4b), Formula (5), Formula (5a), Formula (5b), and Formula (6). Examples of suitable diisocyanates for preparing urethane-extended polythiol adducts include aliphatic diisocyanates and aromatic diisocyanates.

Urethane-extended polythiol adducts can have the structure of Formula (7):

$$HS—(-A-S—C(=O)—NH—R^5—NH—C(=O)—S—)_m-A-SH \qquad (7)$$

wherein,
m is an integer from 1 to 10;
each A independently comprises a moiety having the structure of Formula (6a):

$$-(—R^1—S—R^2—S—)_n—R^1— \qquad (6a)$$

wherein,
n is an integer from 1 to 10;
each $R^1$ independently comprises a structure of Formula (1a):

$$-[—(CHR^3)_p—X—]_q—(CHR^3)_r— \qquad (1a)$$

wherein,
each $R^3$ comprises hydrogen or methyl;
each X is independently selected from O and S;
p is an integer from 2 to 6;
q is an integer from 1 to 5; and
r is an integer from 2 to 10;

each $R^2$ independently comprises a moiety having the structure of Formula (3a):

$$—C(—R^4)_2— \qquad (3a)$$

wherein each $R^4$ independently comprises $C_{1-5}$ alkyl; and
each $R^5$ independently comprises a core of a diisocyanate.

In urethane-extended polythiol adducts of Formula (7), m can be an integer from 1 to 10, from 1 to 8, from 1 to 6, from 1 to 4, or from 1 to 3. In urethane-extended polythiol adducts of Formula (7), m can be 1, 2, 3, 4, 5, 6, 7, 8, 9, or 10.

In urethane-extended polythiol adducts of Formula (7), each A can comprise, for example, a moiety having the structure of Formula (6b), Formula (6c), Formula (6d), or Formula (6e):

$$—S—[—(CH_2)_p—S—]_q—(CH_2)_r—S— \qquad (6b)$$

$$—S—[—(CH_2)_2—O—]_q—(CH_2)_2—S— \qquad (6c)$$

$$—S—[—(CH_2)_2—S—]_q—(CH_2)_2—S— \qquad (6d)$$

$$—S—[—(CH_2)_2)—O—]_q—(CH_2)_2—S— \qquad (6e)$$

where p, q, and r are defined as in Formula (1).

In urethane-extended polythiol adducts of Formula (7), each $R^4$ can independently comprise methyl, ethyl, n-propyl, n-butyl, n-pentyl, isopropyl, sec-butyl, pentan-2-yl, 2-methylbutyl, isopentyl, 3-metylbutan-2-yl, or isobutyl. In urethane-extended polythiol adducts of Formula (7), each $R^4$ can independently comprise methyl or ethyl.

Diisocyanates

Diisocyanates can be used to prepare urethane-extended polythiol adducts and prepolymers of the present disclosure.

For example, urethane-extended polythiol adducts provided by the present disclosure can be prepared by reacting a polythiol adduct with a diisocyanate.

A diisocyanate can comprise an aliphatic diisocyanate, an aromatic diisocyanate, or a combination thereof.

Suitable diisocyanates include aliphatic diisocyanates such as isophorone diisocyanate (IPDI), tetramethyl xylene diisocyanate (TMX), 4,4'-methylene dicyclohexyl diisocyanate ($H_{12}$MDI), methylene diphenyl diisocyanate (MDI), toluene diisocyanate (TDI), hexamethylene diisocyanate (HDI), and a combination of any of the foregoing.

Examples of other suitable aliphatic diisocyanates include 1,6-hexamethylene diisocyanate (HDI), 1,5-diisocyanato-2-methylpentane, methyl-2,6-diisocyanatohexanoate, bis(isocyanatomethyl)cyclohexane, 1,3-bis(isocyanatomethyl)cyclohexane, 2,2,4-trimethylhexane 1,6-diisocyanate, 2,4,4-trimethylhexane 1,6-diisocyanate, 2,5(6)-bis(isocyanatomethyl)cyclo[2.2.1.]heptane, 1,3,3-trimethyl-1-(isocyanatomethyl)-5-isocyanatocyclohexane, 1,8-diisocyanato-2,4-dimethyloctane, octahydro-4,7-methano-1H-indenedimethyl diisocyanate, and 1,1'-methylenebis(4-isocyanatocyclohexane), and 4,4'-methylene dicyclohexyl diisocyanate ($H_{12}$MDI).

Examples of suitable alicyclic aliphatic diisocyanates include isophorone diisocyanate (IPDI), cyclohexane diisocyanate, methylcyclohexane diisocyanate, bis(isocyanatomethyl)cyclohexane, bis(isocyanatocyclohexyl)methane, bis(isocyanatocyclohexyl)-2,2-propane, bis(isocyanatocyclohexyl)-1,2-ethane, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-2-(3-isocyanatopropyl)-5-(2-isocyanatoethyl)-bicyclo[2.2.1]-heptane, and 2-isocyanatomethyl-2-(3-isocyanatopropyl)-6-(2-isocyanatoethyl)-bicyclo[2.2.1]-heptane.

Examples of suitable aromatic diisocyanates in which the isocyanate groups are not bonded directly to the aromatic ring include bis(isocyanatoethyl)benzene, α, α, α',α'-tetramethylxylene diisocyanate, 1,3-bis(1-isocyanato-1-methylethyl)benzene, bis(isocyanatobutyl)benzene, bis(isocyanatomethyl)naphthalene, bis(isocyanatomethyl)diphenyl ether, bis(isocyanatoethyl)phthalate, and 2,5-di(isocyanatomethyl)furan. Aromatic diisocyanates having isocyanate groups bonded directly to the aromatic ring include phenylene diisocyanate, ethylphenylene diisocyanate, isopropylphenylene diisocyanate, dimethylphenylene diisocyanate, diethylphenylene diisocyanate, diisopropylphenylene diisocyanate, naphthalene diisocyanate, methylnaphthalene diisocyanate, biphenyl diisocyanate, 4,4'-diphenylmethane diisocyanate, bis(3-methyl-4-isocyanatophenyl)methane, bis(isocyanatophenyl)ethylene, 3,3'-dimethoxy-biphenyl-4,4'-diisocyanate, diphenylether diisocyanate, bis(isocyanatophenylether)ethyleneglycol, bis(isocyanatophenylether)-1,3-propyleneglycol, benzophenone diisocyanate, carbazole diisocyanate, ethylcarbazole diisocyanate, dichlorocarbazole diisocyanate, 4,4'-diphenylmethane diisocyanate, p-phenylene diisocyanate, 2,4-toluene diisocyanate, and 2,6-toluene diisocyanate.

Additional examples of suitable aromatic diisocyanates include 1,3-phenylene diisocyanate, 1,4-phenylene diisocyanate, 2,6-toluene diisocyanate (2,6-TDI), 2,4-toluene diisocyanate (2,4-TDI), a blend of 2,4-TDI and 2,6-TDI, 1,5-diisocyanato naphthalene, diphenyl oxide 4,4'-diisocyanate, 4,4'-methylenediphenyl diisocyanate (4,4-MDI), 2,4'-methylenediphenyl diisocyanate (2,4-MDI), 2,2'-diisocyanatodiphenylmethane (2,2-MDI), diphenylmethane diisocyanate (MDI), 3,3'-dimethyl-4,4'-biphenylene isocyanate, 3,3'-dimethoxy-4,4'-biphenylene diisocyanate, 1-[(2,4-diisocyanatophenyl)methyl]-3-isocyanato-2-methyl benzene, and 2,4,6-triisopropyl-m-phenylene diisocyanate.

Other examples of suitable diisocyanates include 1,3-phenylene diisocyanate, 1,4-phenylene diisocyanate, 2,6-toluene diisocyanate (2,6-TDI), 2,4-toluene diisocyanate (2,4-TDI), a blend of 2,4-TDI and 2,6-TDI, 1,5-diisocyanato naphthalene, diphenyl oxide 4,4'-diisocyanate, 4,4'-methylenediphenyl diisocyanate (4,4-MDI), 2,4'-methylenediphenyl diisocyanate (2,4-MDI), 2,2'-diisocyanatodiphenylmethane (2,2-MDI), diphenylmethane diisocyanate (MDI), 3,3'-dimethyl-4,4'-biphenylene isocyanate, 3,3'-dimethoxy-4,4'-biphenylene diisocyanate, 1-[(2,4-diisocyanatophenyl)methyl]-3-isocyanato-2-methyl benzene, 2,4,6-triisopropyl-m-phenylene diisocyanate, 4,4-methylene dicyclohexyl diisocyanate (H12MDI), and a combination of any of the foregoing.

A diisocyanate can have the structure of Formula (8):

$$O=C=N-R^5-N=C=O \qquad (8)$$

where $R^5$ represents a core of the diisocyanate such as a core of an aliphatic diisocyanate or an aromatic diisocyanate.

Urethane-extended polythiol adducts can be prepared by reacting a diisocyanate and an un-extended polythiol adduct in the presence of a catalyst such as dibutyl tin dilaurate at high temperature. A urethane-extended polythiol adduct can be solid at room temperature and can be soluble in suitable solvents.

Terminal Modified Polythiol Adducts

Polythiol adducts provided by the present disclosure such as un-extended polythiol adducts of Formula (6) and urethane-extended polythiol adducts of Formula (7) may be modified for use with other chemistries. Terminal modified adducts may comprise terminal epoxy groups, Michael acceptor groups, isocyanate groups, alkenyl groups, hydroxyl groups, polyalkoxysilyl groups.

Isocyanate-Terminated Urethane-Containing Prepolymers

Isocyanate-terminated urethane-containing prepolymers provided by the present disclosure can comprise the reaction product of reactants comprising a polythiol adduct such as a polythiol adduct such as an un-extended polythiol adduct or a urethane-extended polythiol adduct provided by the present disclosure; a thiol-terminated sulfur-containing prepolymer; and a diisocyanate.

A polythiol adduct can comprise any of those disclosed herein, including polythiol adducts of Formula (4), Formula (4a), Formula (4b), Formula (5), Formula (5a), Formula (5b), Formula (6), or a combination of any of the foregoing.

A diisocyanate used to prepare an isocyanate-terminated urethane-containing prepolymer can include any suitable diisocyanate such as any of the diisocyanates disclosed herein, including aliphatic diisocyanates and aromatic diisocyanates.

Thiol-terminated sulfur-containing prepolymers can include thiol-terminated polythioethers, thiol-terminated polysulfides, thiol-terminated sulfur-containing polyformals, or combinations of any of the foregoing. A thiol-terminated sulfur-containing prepolymer can be difunctional, trifunctional, or may have a functionality greater than 3 such as from 4 to 6. A thiol-terminated sulfur-containing prepolymer can include a combination of thiol-terminated sulfur-containing prepolymers having different functionalities such that an average functionality of the thiol-terminated sulfur-containing prepolymer is a non-integer value. For example, the average functionality of a thiol-terminated sulfur-containing prepolymer can be from 2.05 to 2.9, from 2.05 to 2.8 from 2.1 to 2.6, or from 2.1 to 2.4.

A thiol-terminated sulfur-containing prepolymer can comprise a thiol-terminated sulfur-containing prepolymer of Formula (9a), a thiol-terminated sulfur-containing prepolymer of Formula (9b), a thiol-terminated sulfur-containing prepolymer of Formula (9c), or a combination of any of the foregoing:

  (9a)

  (9b)

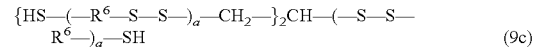  (9c)

wherein,
each P independently comprises a polythioether moiety or a polysulfide moiety;
B represents a core of a z-valent, polyfunctionalizing agent $B(-V)_z$ wherein,
z is an integer from 3 to 6; and
each V is a moiety comprising a terminal group reactive with a thiol;
each —V'— is derived from the reaction of —V with a thiol;
each a is independently an integer from 1 to 50;

the sum of each a is an integer from 3 to 60; and each $R^6$ comprises a moiety having the structure —$(CH_2)_2$—O—$CH_2$—O—$(CH_2)_2$—.

In prepolymers of Formula (9a) and Formula (9b), P can comprise a core or backbone of a polythioether prepolymer or a core or backbone of a polysulfide prepolymer. In prepolymers of Formula (9a) and Formula (9b), P can comprise one or more thioether groups —S— and/or one or more ether groups —O—.

Polythioether Prepolymers

A thiol-terminated sulfur-containing prepolymer can comprise a thiol-terminated polythioether prepolymer comprising a backbone comprising the structure of Formula (10):

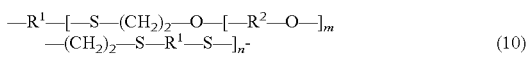

wherein,
- each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a -[—$(CHR^3)$—$]_p$—X—$]_q$—$(CHR^3)_r$— group, wherein each $R^3$ is selected from hydrogen and methyl;
- each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a -[(—$CH_2$—$)_p$—X—$]_q$—$(CH_2)_r$— group;
- each X is independently selected from O, S, —NH—, and —N(—$CH_3$)—;
- m is an integer from 0 to 50;
- n is an integer ranging from 1 to 60;
- p is an integer ranging from 2 to 6;
- q is an integer ranging from 1 to 5; and
- r is an integer ranging from 2 to 10.

For example, P in thiol-terminated sulfur-containing prepolymers of Formula (9a) and Formula (9b) can have the structure of Formula (10).

A thiol-terminated polythioether prepolymer can comprise a thiol-terminated polythioether prepolymer of Formula (11a), a thiol-terminated polythioether prepolymer of Formula (11b), or a combination thereof:

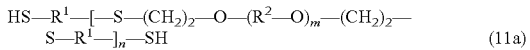

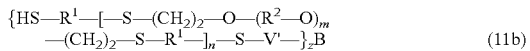

wherein,
- each $R^1$ is independently selected from $C_{2-10}$ alkanediyl, $C_{6-8}$ cycloalkanediyl, $C_{6-14}$ alkanecycloalkanediyl, $C_{5-8}$ heterocycloalkanediyl, and -[(—$CHR^3$—$)_p$—X—$]_q$-(—$CHR^3$—$)_r$-, wherein,
  - p is an integer from 2 to 6;
  - q is an integer from 1 to 5;
  - r is an integer from 2 to 10;
  - each $R^3$ is independently selected from hydrogen and methyl; and
  - each X is independently selected from —O—, —S—, —NH—, and —N(—$CH_3$)—;
- each $R^2$ is independently selected from $C_{1-10}$ alkanediyl, $C_{6-8}$ cycloalkanediyl, $C_{6-14}$ alkanecycloalkanediyl, and -[(—$CHR^3$—$)_p$—X—$]_q$-(—$CHR^3$—$)_r$-, wherein p, q, r, $R^3$, and X are as defined as for $R^1$;
- m is an integer from 0 to 50;
- n is an integer from 1 to 60;
- B represents a core of a z-valent, polyfunctionalizing agent B(—V)$_z$ wherein,
  - z is an integer from 3 to 6; and
  - each V is a moiety comprising a terminal group reactive with a thiol; and
  - each —V'— is derived from the reaction of —V with a thiol.

In thiol-terminated polythioethers of Formula (11a) and in Formula (11b), $R^1$ can be -[(—$CH_2$—$)_p$—X—$]_q$—$(CH_2)_r$—, where p can be 2, X can be —O—, q can be 2, r can be 2, $R^2$ can be ethanediyl, m can be 2, and n can be 9.

In thiol-terminated polythioethers of Formula (11a) and Formula (11b), $R^1$ can be $C_{2-6}$ alkanediyl or -[—$(CHR^3)_s$—X—$]_q$—$(CHR^3)_r$—.

In thiol-terminated polythioethers of Formula (11a) and Formula (11b), $R^1$ can be -[—$(CHR^3)_s$—X—$]_q$—$(CHR^3)_r$—, or X can be —O—, or X can be —S—.

In thiol-terminated polythioethers of Formula (11a) and Formula (11b), $R^1$ can be -[—$(CHR^3)_s$—X—$]_q$—$(CHR^3)_r$—, p can be 2, r can be 2, q can be 1, and X can be —S—; or, p can be 2, q can be 2, r can be 2, and X can be —O—; or p can be 2, r can be 2, q can be 1, and X can be —O—.

In thiol-terminated polythioether prepolymers of Formula (11a) and Formula (11b), $R^1$ can be -[—$(CHR^3)_s$—X—$]_q$—$(CHR^3)_r$—, each $R^3$ can be hydrogen, or at least one $R^3$ is methyl.

In thiol-terminated polythioethers of Formula (11a) and Formula (1 b), each $R^1$ can be the same or at least one $R^1$ can be different.

In thiol-terminated polythioether prepolymers of Formula (11a) and Formula (11b), m can be, for example, an integer from 0 to 50; from 0 to 10, from 1 to 10, or from 2 to 10.

In thiol-terminated polythioether prepolymers of Formula (11a) and Formula (11b), n can be, for example, an integer from 1 to 60; from 1 to 10, from 2 to 10, or from 3 to 10.

A thiol-terminated sulfur-containing prepolymer can comprise a thiol-terminated polythioether prepolymer. Examples of thiol-functional polythioether prepolymers are disclosed, for example, in U.S. Pat. No. 6,172,179, which is incorporated by reference in its entirety. A thiol-functional polythioether prepolymer can comprise Permapol® P3.1E, available from PRC-DeSoto International Inc., Sylmar, Calif.

A thiol-terminated polythioether prepolymer can have, for example, a weight average molecular weight from 1,000 Daltons to 10,000 Daltons, from 2,000 Daltons to 5,000 Daltons, or from 3,000 Daltons to 4,000 Daltons. A thiol-terminated polythioether prepolymer can have an average thiol functionality from 2.05 to 3.0, such as from 2.1 to 2.6.

A thiol-terminated polythioether prepolymer may comprise a mixture of different polythioethers and the polythioethers may have the same or different functionality. A thiol-terminated polythioether prepolymer can have an average functionality from 2 to 6, from 2 to 4, from 2 to 3, or from 2.05 to 2.5. For example, a thiol-terminated polythioether prepolymer can comprise a difunctional sulfur-containing polymer, a trifunctional sulfur-containing polymer, or a combination thereof.

Various methods can be used to prepare thiol-terminated polythioethers of Formula (11a) and Formula (11b). Examples of suitable thiol-terminated polythioethers, and methods for their production, are described in U.S. Pat. No. 6,172,179, which is incorporated by reference in its entirety. Such thiol-terminated polythioethers may be difunctional, that is, linear polymers having two terminal thiol groups, or polyfunctional, that is, branched polymers have three or more terminal thiol groups.

A thiol-terminated polythioether can be prepared by reacting a polythiol and a diene such as a divinyl ether, and the respective amounts of the reactants used to prepare the polythioethers can be chosen to yield terminal thiol groups. Thus, in some cases, (n or >n, such as n+1) moles of a polythiol, such as a dithiol or a mixture of at least two different dithiols and about 0.05 moles to 1 moles, such as 0.1 moles to 0.8 moles, of a thiol-terminated polyfunctionalizing agent may be reacted with (n) moles of a diene, such as a divinyl ether, or a mixture of at least two different dienes, such as a combination of divinyl ether. A thiol-terminated polyfunctionalizing agent can be present in the reaction mixture in an amount sufficient to provide a thiol-terminated polythioether having an average functionality from 2.05 to 3, such as 2.1 to 2.8.

A reaction used to make a thiol-terminated polythioether may be catalyzed by a free radical catalyst. Suitable free radical catalysts include azo compounds, for example azo-bisnitrile compounds such as azo(bis)isobutyronitrile (AIBN); organic peroxides, such as benzoyl peroxide and tert-butyl peroxide; and inorganic peroxides, such as hydrogen peroxide. The reaction can also be effected by irradiation with ultraviolet light either with or without a radical initiator/photosensitizer. Ionic catalysis methods, using either inorganic or organic bases, e.g., triethylamine, may also be used.

Suitable thiol-terminated polythioethers may be produced by reacting a divinyl ether or a mixture of divinyl ethers with a molar excess of dithiol or a molar excess of a mixture of dithiols.

Thus, a thiol-terminated polythioether can comprise the reaction product of reactants comprising:

(a) a dithiol of Formula (12):

wherein,
$R^1$ is selected from $C_{2-6}$ alkanediyl, $C_{6-8}$ cycloalkanediyl, $C_{6-10}$ alkanecycloalkanediyl, $C_{5-8}$ heterocycloalkanediyl, and $-[-(CHR^3)_p-X-]_q-(CHR^3)_r-$;
wherein,
each $R^3$ is independently selected from hydrogen and methyl;
each X is independently selected from $-O-$, $-S-$, $-NH-$, and $-N(-CH_3)-$;
p is an integer from 2 to 6;
q is an integer from 1 to 5; and
r is an integer from 2 to 10; and (b) a divinyl ether of Formula (13):

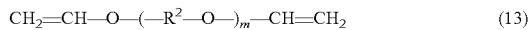

wherein,
each $R^2$ is independently selected from $C_{1-10}$ alkanediyl, $C_{6-8}$ cycloalkanediyl, $C_{6-14}$ alkanecycloalkanediyl, and $-[(-CHR^3-)_p-X-]_q-(-CHR^3-)_r-$, wherein p, q, r, $R^3$, and X are as defined above; and
m is an integer from 0 to 50.

The reactants used to prepare a thiol-terminated polythioether may also comprise (c) a polyfunctional compound such as a polyfunctional compound $B(-V)_z$, where B, $-V$, and z are as defined herein.

Dithiols suitable for use in preparing thiol-terminated polythioethers include those having the structure of Formula (12), other dithiols disclosed herein, or combinations of any of the dithiols disclosed herein. For example, a dithiol has the structure of Formula (12):

wherein,
$R^1$ is selected from $C_{2-6}$ alkanediyl, $C_{6-8}$ cycloalkanediyl, $C_{6-10}$ alkanecycloalkanediyl, $C_{5-8}$ heterocycloalkanediyl, and $-[-(CHR^3)_p-X-]_q-(CHR^3)_r-$;
wherein,
each $R^3$ is independently selected from hydrogen and methyl;
each X is independently selected from $-O-$, $-S-$, and $-NR-$ wherein R is selected from hydrogen and methyl;
p is an integer from 2 to 6;
q is an integer from 1 to 5; and
r is an integer from 2 to 10.

In dithiols of Formula (12), $R^1$ can be $-[-(CHR^3)_p-X-]_q-(CHR^3)_r-$.

In dithiols of Formula (12), X can be $-O-$ or $-S-$, and thus $-[-(CHR^3)_p-X-]_q-(CHR^3)_r-$ in Formula (12) can be $-[(-CHR^3-)_p-O-]_q-(CHR^3)_r-$ or $-[(-CHR^3_2-)_p-S-]_q-(CHR^3)_r-$. P and r can be the same, such as where p and r are both two.

In dithiols of Formula (12), $R^1$ can be selected from $C_{2-6}$ alkanediyl and $-[-(CHR^3)_p-X-]_q-(CHR^3)_r-$.

In dithiols of Formula (12), $R^1$ can be $-[-(CHR^3)_p-X-]_q-(CHR^3)_r-$, and X can be $-O-$, or X can be $-S-$.

In dithiols of Formula (12), $R^1$ can be $-[-(CHR^3)_p-X-]_q-(CHR^3)_r-$, p can be 2, r can be 2, q can be 1, and X can be $-S-$; or p can be 2, q can be 2, r can be 2, and X can be $-O-$; or p can be 2, r can be 2, q can be 1, and X can be $-O-$.

In dithiols of Formula (12), $R^1$ can be $-[-(CHR^3)_p-X-]_q-(CHR^3)_r-$, each $R^3$ can be hydrogen, or at least one $R^3$ can be methyl.

In dithiols of Formula (12), each $R^1$ can be derived from dimercaptodioxaoctane (DMDO) or each $R^1$ can be derived from dimercaptodiethylsulfide (DMDS).

In dithiols of Formula (12), each p can independently be selected from 2, 3, 4, 5, and 6; or each p can be the same and can be 2, 3, 4, 5, or 6.

In dithiols of Formula (12), each q can independently be selected from 1, 2, 3, 4, and 5; or each q can be the same and can be 2, 3, 4, or 5.

In dithiols of Formula (12), each r can independently be selected from 2, 3, 4, 5, 6, 7, 8, 9, or 10; or each r can be the same and can be 2, 3, 4, 5, 6, 7, 8, 9, or 10.

Examples of suitable dithiols include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A dithiol may have one or more pendent groups selected from a lower (e.g., $C_{1-6}$) alkyl group, a lower alkoxy group, and a hydroxy group. Suitable alkyl pendent groups include, for example, $C_{1-6}$ linear alkyl, $C_{3-6}$ branched alkyl, cyclopentyl, and cyclohexyl.

Other examples of suitable dithiols include dimercaptodiethylsulfide (DMDS) (in Formula (12), $R^1$ is $-[(-CH_2-)_p-X-]_q-(CH_2)_r-$, wherein p is 2, r is 2, q is 1, and X is —S—); dimercaptodioxaoctane (DMDO) (in Formula (12), $R^1$ is -[(—CH$_2$—)$_p$—X—]$_q$—(CH$_2$)$_r$—, wherein p is 2, q is 2, r is 2, and X is —O—); and 1,5-dimercapto-3-oxapentane (in Formula (12), $R^1$ is -[(—CH$_2$—)$_p$—X—]$_q$—(CH$_2$)$_r$—, wherein p is 2, r is 2, q is 1, and X is —O—). It is also possible to use dithiols that include both heteroatoms in the carbon backbone and pendent alkyl groups, such as methyl groups. Such compounds include, for example, methyl-substituted DMDS, such as HS—CH$_2$CH(CH$_3$)—S—CH$_2$CH$_2$—SH, HS—CH(CH$_3$)CH$_2$—S—CH$_2$CH$_2$—SH and dimethyl-substituted DMDS, such as HS—CH$_2$CH(CH$_3$)—S—CHCH$_3$CH$_2$—SH and HS—CH(CH$_3$)CH$_2$—S—CH$_2$CH(CH$_3$)—SH.

Suitable divinyl ethers for preparing polythioethers include, for example, divinyl ethers of Formula (13):

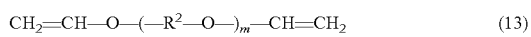

where $R^2$ in Formula (13) is selected from a $C_{2-6}$ n-alkanediyl group, a $C_{3-6}$ branched alkanediyl group, a $C_{6-8}$ cycloalkanediyl group, a $C_{6-10}$ alkanecycloalkanediyl group, and -[(—CH$_2$—)$_p$—O—]$_q$-(—CH$_2$—)$_r$-, where p is an integer ranging from 2 to 6, q is an integer from 1 to 5, and r is an integer from 2 to 10. In a divinyl ether of Formula (13), $R^2$ can be a $C_{2-6}$ n-alkanediyl group, a $C_{3-6}$ branched alkanediyl group, a $C_{6-8}$ cycloalkanediyl group, a $C_{6-10}$ alkanecycloalkanediyl group, and in or -[(—CH$_2$—)$_p$—O—]$_q$-(—CH$_2$—)$_r$—.

In divinyl ethers of Formula (13), each m can independently be an integer from 1 to 3, each m can be the same and can be 1, 2, or 3.

Suitable divinyl ethers include, for example, compounds having at least one oxyalkanediyl group, such as from 1 to 4 oxyalkanediyl groups, i.e., compounds in which m in Formula (13) is an integer ranging from 1 to 4. In divinyl ethers of Formula (13) m can be an integer ranging from 2 to 4. It is also possible to employ commercially available divinyl ether mixtures that are characterized by a non-integral average value for the number of oxyalkanediyl units per molecule. Thus, m in Formula (13) can also take on rational number values ranging from 0 to 10.0, such as from 1.0 to 10.0, from 1.0 to 4.0, or from 2.0 to 4.0.

Examples of suitable divinyl ethers include, divinyl ether, ethylene glycol divinyl ether (EG-DVE) ($R^2$ in Formula (13) is ethanediyl and m is 1), butanediol divinyl ether (BD-DVE) ($R^2$ in Formula (13) is butanediyl and m is 1), hexanediol divinyl ether (HD-DVE) ($R^2$ in Formula (13) is hexanediyl and m is 1), diethylene glycol divinyl ether (DEG-DVE) ($R^2$ in Formula (13) is ethanediyl and m is 2), triethylene glycol divinyl ether ($R^2$ in Formula (13) is ethanediyl and m is 3), tetraethylene glycol divinyl ether ($R^2$ in Formula (13) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such polyvinyl ether monomers. A polyvinyl ether may have one or more pendent groups selected from alkyl groups, hydroxy groups, alkoxy groups, and amine groups.

Divinyl ethers in which $R^2$ in Formula (13) is $C_{3-6}$ branched alkanediyl may be prepared by reacting a polyhydroxy compound with acetylene. Examples of divinyl ethers of this type include compounds in which $R^2$ in Formula (13) is an alkyl-substituted methanediyl group such as —CH(—CH$_3$)—, for which $R^2$ in Formula (13) is ethanediyl and m is 3.8 or an alkyl-substituted ethanediyl.

Other useful divinyl ethers include compounds in which $R^2$ in Formula (13) is polytetrahydrofuryl (poly-THF) or polyoxyalkanediyl, such as those having an average of about 3 monomer units.

Two or more types of divinyl ether monomers of Formula (13) may be used. Thus, two dithiols of Formula (12) and one divinyl ether monomer of Formula (13), one dithiol of Formula (12) and two divinyl ether monomers of Formula (13), two dithiols of Formula (12) and two divinyl ether monomers of Formula (13), and more than two compounds of one or both Formula (12) and Formula (13), may be used to produce a variety of thiol-terminated polythioethers.

A divinyl ether monomer can comprise 20 to less than 50 mole percent of the reactants used to prepare a thiol-terminated polythioether, or 30 mole percent to less than 50 mole percent.

Relative amounts of dithiols and divinyl ethers can be selected to yield polythioethers having terminal thiol groups. Thus, a dithiol of Formula (12) or a mixture of at least two different dithiols of Formula (12), can be reacted with of a divinyl ether of Formula (13) or a mixture of at least two different divinyl ethers of Formula (13) in relative amounts such that the molar ratio of thiol groups to alkenyl groups is greater than 1:1, such as from 1.1 to 2.0:1.0.

The reaction between dithiols and divinyl ethers and/or polythiols and polyvinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be a free-radical catalyst, an ionic catalyst, or ultraviolet radiation. A catalyst does not comprise acidic or basic compounds, and does not produce acidic or basic compounds upon decomposition. Examples of free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts include alkyl peroxides, such as t-butyl peroxide. The reaction may also be effected by irradiation with ultraviolet light either with or without a cationic photoinitiating moiety.

Thiol-terminated polythioethers provided by the present disclosure may be prepared by combining at least one dithiol of Formula (12) and at least one divinyl ether of Formula (13) followed by addition of an appropriate catalyst, and carrying out the reaction at a temperature from 30° C. to 120° C., such as 70° C. to 90° C., for a time from 2 hours to 24 hours, such as 2 hours to 6 hours.

Thiol-terminated polythioethers may comprise a polyfunctional polythioether, i.e., may have an average functionality of greater than 2.0. Suitable polyfunctional thiol-terminated polythioethers include, for example, those having the structure of Formula (11b):

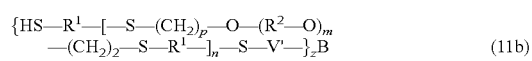

wherein z has an average value of greater than 2.0, a value between 2 and 3, a value between 2 and 4, a value between 3 and 6, or an integer from 3 to 6.

Polyfunctionalizing agents suitable for use in preparing such polyfunctional thiol-terminated polymers include trifunctionalizing agents, that is, compounds where z is 3. Suitable trifunctionalizing agents include, for example, triallyl cyanurate (TAC), 1,2,3-propanetrithiol, isocyanurate-containing trithiols, and combinations thereof, as disclosed in U.S. Application Publication No. 2010/0010133 and in U.S. Application Publication No. 2011/0319559, each of which is incorporated by reference in its entirety. Other useful polyfunctionalizing agents include trimethylolpropane trivinyl ether, and the polythiols described in U.S. Pat. Nos. 4,366,307; 4,609,762; and 5,225,472, each of which is incorporated by reference in its entirety. Mixtures of polyfunctionalizing agents may also be used. As a result, polythioethers provided by the present disclosure may have a wide range of average functionality. For example, trifunctionalizing agents may afford average functionalities from 2.05 to 3.0, such as from 2.1 to 2.6. Wider ranges of average functionality may be achieved by using tetrafunctional or higher functionality polyfunctionalizing agents. Functionality may also be determined by factors such as stoichiometry, as will be understood by those skilled in the art.

A polythioether prepolymer can have, for example, from 8 to 200 —(CH$_2$)$_2$—S—(CH$_2$)$_2$— linkages. A thiol-terminated polythioether prepolymer can have an average molecular weight from 1,000 Daltons to 10,000 Daltons, from 2,000 Daltons to 5,000 Daltons, or from 3,000 Daltons to 4,000 Daltons. A thiol-terminated polythioether prepolymer can have an average functionality, for example, from 2.05 to 3.0 or from 2.1 to 2.6.

Thiol-Terminated Polysulfides

A thiol-terminated sulfur-containing prepolymer can comprise a thiol-terminated polysulfide.

A polysulfide refers to a prepolymer that contains one or more sulfide linkages, i.e., —S$_x$— linkages, where x can be, for example, from 2 to 4, or from 2 to 6, in the polymer backbone and/or in pendent positions on the polymer chain. A polysulfide prepolymer can have two or more sulfur-sulfur linkages, such as —S—S—. Suitable thiol-terminated polysulfides are commercially available, for example, from Akzo Nobel and Toray Fine Chemicals under the names Thiokol®-LP and Thioplast®, respectively. Thioplast® products are available in a wide range of molecular weights ranging, for example, from less than 1,100 to over 8,000, with molecular weight being the average molecular weight in grams per mole. In some cases, a thiol-terminated polysulfide has a number average molecular weight of 1,000 Daltons to 4,000 Daltons. A thiol-terminated polysulfide prepolymer can comprise a Thiokol-LP® polysulfide, a Thioplast® polysulfide, or a combination thereof. The cross-link density of these products can also vary, depending on the amount of crosslinking agent used. The —SH content, i.e., thiol or mercaptan content, of these products can also vary. The mercaptan content and molecular weight of a polysulfide can affect the cure speed of the prepolymer, with cure speed increasing with molecular weight. Examples of suitable thiol-terminated polysulfide prepolymers are disclosed, for example, in U.S. Pat. Nos. 4,623,711, 6,172,179, 6,509,418, 7,009,032, and 7,879,955, each of which is incorporated by reference in its entirety.

Thioplast® polysulfides result from the poly-condensation of bis-(2-chloroethyl-)formal with alkali polysulfide. This reaction generates long-chain macromolecules which can then be cleaved to a required chain length by reductive splitting with sodium dithionate. The disulfide groups are at the same time converted into reactive thiol terminal groups. By introducing a trifunctional component such as 1,2,3-trichloropropane during the synthesis, a third thiol terminal group can be added to a specific number of Thioplast® molecules to establish the extent of cross-linking during the curing process. The value for n may vary, for example, between 7 and 38 depending on the amount of the cleaving agent used. For certain applications, chain length and branching will have to be varied.

A thiol-terminated polysulfide prepolymer can have an average thiol functionality, for example, from 2.1 to 2.5 or from 2.01 to 2.1. A thiol-terminated polysulfide prepolymer can have a weight average molecular weight from 1,000 Daltons to 8,000 Daltons, or from 1,000 Daltons to 5,000 Daltons, an can have a low degree of branching. A thiol-terminated polysulfide prepolymer can have a degree of branching, for example, from 0 to 4, from 0 to 3, from 0 to 2.5, or from 0 to 2.0, where the degree of branching is expressed as mole percent of branching with respect to the prepolymer backbone.

A thiol-terminated sulfur-containing prepolymer can comprise, for example, a thiol-terminated polysulfide having the structure of Formula (9c):

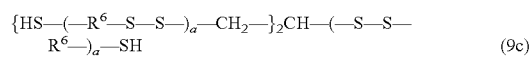

(9c)

wherein, each a is independently an integer from 1 to 50;

the sum of each a is an integer from 5 to 60; and each R$^6$ comprises a moiety having the structure 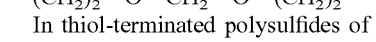

In thiol-terminated polysulfides of Formula (9c), each a can be an integer from 1 to 50, such as from 5 to 35, from 5 to 20, or from 1 to 10. In thiol-terminated polysulfides of Formula (9c), the sum of each can, for example, be from 5 to 60, from 10 to 40, or from 13 to 38. For example, in thiol-terminated polysulfides of Formula (9c), each a can be 6 (Thiokol® LP-3) or each a can be 23 (Thiokol® LP-23).

A thiol-terminated polysulfide prepolymer can be difunctional, trifunctional, have a higher functionality than three, or may be a combination of different functionalities. A thiol-terminated polysulfide prepolymer can be a trifunctional thiol-terminated polysulfide, including a mixture of trifunctional thiol-terminated polysulfides.

A thiol-terminated polysulfide can comprise, for example, Thiokol® LP-3, Thiokol® LP-32, or a combination thereof. A thiol-terminated polysulfide can have a mole percent (%) thiol content from 1 to 7, an average molecular weight from 1,100 Daltons to 6,500 Daltons, a mole percent (%) sulfur content of 37 to 38, and from 0.2 mol % to 2 mol % of a polyfunctionalizing agent A thiol-terminated polysulfide can comprise bis(ethyleneoxy)methane containing disulfide linkages.

A thiol-terminated polysulfide can have an average thiol functionality from 2 to 2.5, from 2 to 2.4, from 2 to 2.3, from 2 to 2.2, or from 2 to 2.1. A thiol-terminated polysulfide can have an average molecular weight from 1,000 Daltons to 8,000 Daltons, from 1,000 Daltons to 6,000 Daltons, from 1,000 Daltons to 5,000 Daltons, or from 1,000 to 3,000 Daltons. Thiol-terminated polysulfides can be characterized by an average low degree of branching such as from 0 to 4, from 0 to 3, from 0 to 2.5, or from 0 to 2.0, where the degree of branching is expressed as mole percent of branches per mole of polysulfide backbone.

Thiol-Terminated Sulfur-Containing Polyformals

Sulfur-containing polyformal prepolymers useful in aerospace sealant applications are disclosed, for example, in U.S. Application Publication No. 2012/0234205 and in U.S. Application Publication No. 2012/0238707, each of which is incorporated by reference in its entirety.

Isocyanate-Terminated Urethane-Containing Prepolymers

Isocyanate-terminated urethane-containing prepolymers can comprise the reaction product of reactants comprising a thiol-terminated sulfur-containing prepolymer, a polythiol adduct, and a diisocyanate.

In general it is desirable that isocyanate-terminated urethane-containing prepolymers provided by the present disclosure have a low viscosity such as less than 10 Poise, less than 25 Poise, less than 50 Poise, or less than 100 Poise. The use of low viscosity prepolymers facilitates the use of less solvent in a composition. For example, it can be desirable that a composition contain less than 5 wt % solvent or less than 10 wt % solvent. The use of low solvent content can lead to less shrinkage of an applied coating. Isocyanate-terminated urethane-containing prepolymers provided by the present disclosure can also have a viscosity greater than 100 Poise, such as, for example, from 100 Poise to 500 Poise.

A thiol-terminated sulfur-containing prepolymers can comprise a thiol-terminated polythioether, a thiol-terminated polysulfide, a thiol-terminated sulfur-containing polyformal, or a combination of any of the foregoing. A polythiol adduct can comprise an un-extended polythiol adduct, a urethane-extended polythiol adduct, or a combination thereof. A diisocyanate can include an aliphatic diisocyanate, an aromatic diisocyanate, or a combination thereof, including any of the diisocyanates disclosed herein.

An isocyanate-terminated urethane-containing prepolymer can comprise an isocyanate-terminated urethane-containing prepolymer of Formula (15a), an isocyanate-terminated urethane-containing prepolymer of Formula (15b), or a combination thereof:

D-S—P—S-D (15a)

{D-S—P—S—V'—}$_z$B (15b)

wherein,
each D independently can comprise a moiety having the structure of Formula (16a), Formula (16b), Formula (16c), Formula (16d), Formula (16e), Formula (16f), or Formula (16g):

—C(=O)—NH—R$^5$—N=C=O (16a)

—C(=O)—NH—R$^5$—[—NH—C(=O)—S-E-S—C(=O)—NH—R$^5$—]$_m$—N=C=O (16b)

—C(=O)—NH—R$^5$—[—NH—C(=O)—S-E-S—C(=O)—NH—R$^5$—]$_m$—NH—C(=O)—S—P—S—V'—B{—V'—S—P—S—C(=O)—NH—R$^5$—N=C=O}$_{z-1}$ (16c)

—C(=O)—NH—R$^5$—{—NH—C(=O)—S-E-S—C(=O)—NH—R$^5$—}$_m$—NH—C(=O)—S—P—S—V'—B{—V'—S—P—S—C(=O)—NH—R$^5$—[—NH—C(=O)—S-E-S—C(=O)—NH—R$^5$—]$_m$—N=C=O}$_{z-1}$ (16d)

—C(=O)—NH—R$^5$—NH—C(=O)—S—P—S—V'—B{—V'—S—P—S—C(=O)—NH—R$^5$—N=C=O}$_{z-1}$ (16e)

—C(=O)—NH—R$^5$—NH—C(=O)—S—P—S—V'—B{—V'—S—P—S—C(=O)—NH—R$^5$—[—NH—C(=O)—S-E-S—C(=O)—NH—R$^5$—]$_m$—N=C=O}$_{z-1}$ (16f)

—C(=O)—NH—R$^5$—[—NH—C(=O)—S-E-S—C(=O)—NH—R$^5$—]$_m$—NH—C(=O)—S—P—S—V'—B{—V'—S—P—S—C(=O)—NH—R$^5$—[—NH—C(=O)—S-E-S—C(=O)—NH—R$^5$—]$_m$—N=C=O}$_{z-1}$ (16g)

wherein,
each R$^5$ independently comprises a core of a diisocyanate;
each m is an integer from 1 to 10;
each E comprises a core of a polythiol adduct;
each P comprises a polythioether moiety or a polysulfide moiety;
B represents a core of a z-valent, polyfunctionalizing agent B(—V)$_z$ wherein,
z is an integer from 3 to 6; and
each V is a moiety comprising a terminal group reactive with a thiol; and
each —V'— is derived from the reaction of —V with a thiol.

In isocyanate-terminated urethane-containing prepolymers of Formula (15a) and Formula (15b), each E can independently comprise a moiety having the structure of Formula (6a) or Formula (7a):

-(—R$^1$—S—R$^2$—S—)$_n$—R$^1$— (6a)

-(-A-S—C(=O)—NH—R$^5$—NH—C(=O)—S—)$_m$-A- (7a)

wherein,
each A independently comprises a moiety having the structure of Formula (6a);
n is an integer from 1 to 10;
each R$^1$ independently comprises a structure of Formula (1a):

-[—(CHR$^3$)$_p$—X—]$_q$—(CHR$^3$)$_r$— (1a)

wherein,
each R$^3$ is independently selected from hydrogen and methyl;
each X is independently selected from O and S;
p is an integer from 2 to 6;
q is an integer from 1 to 5; and
r is an integer from 2 to 10;
each R$^2$ independently comprises a moiety having the structure of Formula (3a):

—C(—R$^4$)$_2$— (3a)

where each R$^4$ independently comprises C$_{1-5}$ alkyl; and
each R$^5$ is a core of a diisocyanate.

In isocyanate-terminated urethane-containing prepolymers of Formula (15a) and Formula (15b), each P can comprise a moiety of Formula (11c) or a moiety of Formula (18):

—R$^1$—[—S—(CH$_2$)$_2$—O—(R$^2$—O)$_m$—(CH$_2$)$_2$—S—R$^1$—]$_n$- (11c)

—(CH$_2$)$_2$—O—CH$_2$—O—(CH$_2$)$_2$— (18)

where m, n, R$^1$ and R$^2$ are defined as for Formula (11a).

An isocyanate-terminated urethane-containing prepolymer can have the structure of the Formula (19):

{D-S-}$_3$G (19)

wherein,
G is a moiety of Formula (9d):

{-(—R$^6$—S—S—)$_a$—CH$_2$—}$_2$CH—(—S—S—R$^6$—)$_a$- (9d)

wherein,
each a is independently an integer from 1 to 50;
the sum of each a is an integer from 5 to 60; and each $R^6$ comprises a moiety having the structure —$(CH_2)_2$—O—$CH_2$—O—$(CH_2)_2$—; and each D independently can comprise a moiety having the structure of Formula (20a), Formula (20b), Formula (20c) or Formula (20d):

—C(=O)—NH—$R^5$—N=C=O (20a)

—C(=O)—NH—$R^5$—[—NH—C(=O)—S-E-S—C(=O)—NH—$R^5$—]$_m$—N=C=O (20b)

—C(=O)—NH—$R^5$—NH—C(=O)—S-G{-S-D'}$_2$ (20c)

—C(=O)—NH—$R^5$—[—NH—C(=O)—S-E-S—C(=O)—NH—$R^5$—]$_m$—NH—C(=O)—S-G{-S-D'}$_2$ (20d)

wherein,
each $R^5$ independently comprises a core of a diisocyanate;
each m is an integer from 1 to 10;
each E comprises a core of a polythiol adduct; and
each D' comprises a moiety of Formula (20a) or a moiety of Formula (20b).

In the polyaddition reaction between a thiol-terminated sulfur-containing prepolymer, a polythiol adduct and a diisocyanate, the reactants can comprise an equivalent ratio of thiol-terminated sulfur-containing prepolymer from about 2:5 to about 1.5:4, from about 1:3 to about 1:5, or about 1:3. The total diisocyanate equivalent to thiol equivalent index can be from about 2.0 to about 2.1, and the equivalent ratio of diisocyanate to thiol can be from about 5:1 to about 2:1. The equivalent ratio can also be selected to provide a urethane-containing prepolymer comprising terminal thiol groups. The equivalent ratio can also be selected to provide a urethane-containing prepolymer comprising terminal isocyanate groups.

An isocyanate-terminated urethane-containing prepolymer provided by the present disclosure can also comprise the reaction product of reactants comprising an isocyanate-terminated sulfur-containing prepolymer, a polythiol adduct, and a diisocyanate; where the isocyanate-terminated sulfur-containing prepolymer can comprise the reaction product of reactants comprising a diisocyanate and a thiol-terminated sulfur-containing prepolymer.

For example, a thiol-terminated polysulfide or combination of thiol-terminated polysulfides can be reacted with a diisocyanate such as an aliphatic diisocyanate or an aromatic diisocyanate to provide an isocyanate-terminated polysulfide. An isocyanate-terminated polysulfide may first be prepared and then combined with a polythiol adduct provided by the present disclosure and a diisocyanate to provide an isocyanate-terminated urethane-containing prepolymer.

Examples of suitable isocyanate-terminated polysulfides include those derived from Thiokol®-LP polysulfides, which can comprise isocyanate-terminated polysulfides having the structure of Formula (20):

{O=C=N—$R^5$—NH—C(=O)—S—[—$(CH_2)_2$—O—$CH_2$—O—$(CH_2)_2$—S—S—]$_a$—$(CH_2)_2$—}$_2$CH—[—S—S—O—$CH_2$—O—$(CH_2)_2$—]$_n$—S—C(=O)—NH—$R^5$—N=C=O (20)

where each $R^5$ comprises a core of a diisocyanate such as a core of an aliphatic or an aromatic diisocyanate, and n can be an integer from 1 to 50, such as from 5 to 35.

For example, in isocyanate-terminated polysulfides of Formula (20), n can be 6 (Thiokol® LP-3) or n can be 23 (Thiokol® LP-23). In addition to isocyanate-terminated polysulfides of Formula (20), isocyanate-terminated polysulfides can comprise isocyanate-terminated polysulfides in which two or more polyfunctional polysulfides are bonded together via a diisocyanate.

An isocyanate-terminated urethane-containing polysulfide can be prepared by reacting a thiol-terminated polysulfide and a diisocyanate in the presence of a tin catalyst.

An isocyanate-terminated sulfur-containing prepolymer can comprise an isocyanate-terminated polythioether of Formula (21a), an isocyanate-terminated polythioether of Formula (21b), or a combination thereof:

$R^6$—S—$R^1$—[—S—$(CH_2)_2$—O—$(R^2$—O)$_m$—$(CH_2)_2$—S—$R^1$—]$_n$—S—$R^6$ (21a)

{$R^6$—S—$R^1$—[—S—$(CH_2)_2$—O—$(R^2$—O)$_m$—$(CH_2)_2$—S—$R^1$—]$_n$—S—V'—}$_z$B (21b)

wherein,
each $R^1$ independently is selected from $C_{2-10}$ alkanediyl, $C_{6-8}$ cycloalkanediyl, $C_{6-14}$ alkanecycloalkanediyl, $C_{5-8}$ heterocycloalkanediyl, and -[(—$CHR^3$—)$_p$—X—]$_q$-(—$CHR^3$—)$_r$-, wherein,
p is an integer from 2 to 6;
q is an integer from 1 to 5;
r is an integer from 2 to 10;
each $R^3$ is independently selected from hydrogen and methyl; and
each X is independently selected from —O—, —S—, —NH—, and —N(—$CH_3$)—;
each $R^2$ is independently selected from $C_{1-10}$ alkanediyl, $C_{6-8}$ cycloalkanediyl, $C_{6-14}$ alkanecycloalkanediyl, and -[(—$CHR^3$—)$_p$—X—]$_q$-(—$CHR^3$—)$_r$-, wherein p, q, r, $R^3$, and X are as defined as for $R^1$;
m is an integer from 0 to 50;
n is an integer from 1 to 60;
B represents a core of a z-valent, polyfunctionalizing agent B(—V)$_z$ wherein,
z is an integer from 3 to 6; and
each V is a moiety comprising a terminal group reactive with a thiol; and
each —V'— is derived from the reaction of —V with a thiol; and
each $R^6$ independently comprises a moiety having the structure of Formula (22):

—C(=O)—NH—$R^5$—N=C=O (22)

wherein $R^5$ comprises a core of a diisocyanate.

An isocyanate-terminated polythioether prepolymer of Formula (11a), Formula (11b), or a combination thereof, can be reacted with a diisocyanate and a polythiol adduct. These reactants can provide, for example, isocyanate-terminated urethane-containing polythioethers of Formula (23a) and Formula (23b):

$R^7$—S—$R^1$—[—S—$(CH_2)_2$—O—$(R^2$—O)$_m$—$(CH_2)_2$—S—$R^1$—]$_n$—S—$R^7$ (23a)

{$R^7$—S—$R^1$—[—S—$(CH_2)_2$—O—$(R^2$—O)$_m$—$(CH_2)_2$—S—$R^1$—]$_n$—S—V'—}$_z$B (23b)

wherein,
each $R^7$ can independently be a moiety of Formula (24):

—C(=O)—NH—$R^5$—[—NH—C(=O)—S-E-S—C(=O)—NH—$R^5$—]$_m$—N=C=O (24)

wherein,
each E independently can comprise a moiety having the structure of Formula (6a) or Formula (7a):

-(—R¹—S—R²—S—)ₙ—R¹—   (6a)

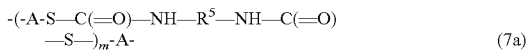

-(-A-S—C(=O)—NH—R⁵—NH—C(=O)
—S—)ₘ-A-   (7a)

where n, m, z, R¹, R², R⁵, and R⁷ are defined as in Formula (6) and Formula (7), and A is a moiety of Formula (7a).

An isocyanate-terminated sulfur-containing prepolymer can comprise an isocyanate-terminated polysulfide having the structure of Formula (25):

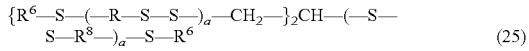

{R⁶—S—(—R—S—S—)ₐ—CH₂—}₂CH—(—S—S—R⁸—)ₐ—S—R⁶   (25)

wherein, each a can independently be an integer from 1 to 60;
the sum of each a can be an integer from 3 to 60;
each R⁵ comprises a moiety having the structure —(CH₂)₂—O—CH₂—O—(CH₂)₂—; and
each R⁶ independently comprises a moiety having the structure of Formula (22):

—C(=O)—NH—R⁵—N=C=O   (22)

where R⁵ comprises the core of a diisocyanate.

Monomeric Polythiols

In addition to a thiol-terminated sulfur-containing prepolymer, the reactants used to from an isocyanate-terminated urethane-containing prepolymer provided by the present disclosure can include a monomeric polythiol. Monomeric polythiols include low molecular weight polythiols and can be used to control the hard segment and soft segment content of the polymer chain. Suitable monomeric polythiols include, for example, pentaerythritol tetra(3-mercaptopropionate), trimethylpropane-tri(3-mercaptopropionate), glycol-di(3-mercaptopropionate) or propylene glycol (3-mercaptopropionate). Suitable monomeric polythiols and their use in polyurethane compositions are disclosed, for example, in International Publication No. WO 2009/095739, which is incorporated by reference in its entirety.

Compositions

Compositions can comprise an isocyanate-terminated urethane-containing prepolymer provided by the present disclosure. A composition can further comprise a curing agent such as a polyamine, a catalyst, a filler such as a low density filler, adhesion promoters, pigments, other additives, or combinations of any of the foregoing.

Compositions may also employ alternative curing chemistries. For example, a composition may employ an epoxy/amine curing chemistry. In such compositions an isocyanate-terminated urethane-containing prepolymer may be modified to comprise terminal epoxy group by reacting an isocyanate-terminated urethane-containing prepolymer with an epoxide alcohol such as 2,3-epoxy-1-propanol (glycidol) to provide an epoxy-terminated urethane-containing prepolymer. The epoxy-terminated urethane-containing prepolymer may be combined with a polyamine curing agent.

Polyamine

Compositions provided by the present disclosure can include a curing agent such as a polyamine curing agent or a polyepoxide curing agent.

A polyamine curing agent can comprise a polyamine such as a diamine, triamine or combination thereof. A diamine can comprise a cycloaliphatic diamine. A cycloaliphatic diamine can comprise, for example, N-isopropyl-2-((isopropylamino) ethyl)-3,5,5-trimethylcyclohexan-1-amine, 4,4'-methylenebis(N-(sec-butyl)cyclohexan-1-amine), or a combination of any of the foregoing.

A polyamine suitable for use in compositions provided by the present disclosure can include polyetheramines such as Jeffamine® polyetheramines (Huntsman). Suitable polyetheramines are also available from BASF. Polyetheramines contain primary amino groups attached to the end of a polyether backbone. The polyether backbone can be based on propylene oxide, ethylene oxide, or a combination thereof. Polyetheramines can be used as curing agent in sealant compositions.

A suitable aliphatic diamine can comprise Jefflink® 754, Clearlink® 1000, or a combination thereof.

Suitable aliphatic diamine curing agents can also include any of those disclosed in U.S. Pat. No. 6,403,752, such as diamines of Formula (8), Formula (9), Formula (10), Formula (11), and Formula (12):

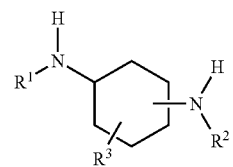

(8)

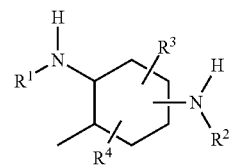

(9)

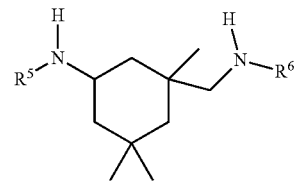

(10)

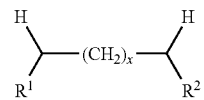

(11)

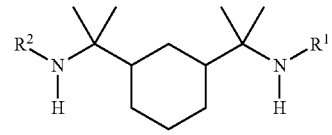

(12)

where x is an integer from 2 to 20; each of R¹ and R² are independently $C_{1-20}$ alkyl; each of R⁵ and R⁶ are independently $C_{4-20}$ alkyl; and each of R³ and R⁴ are hydrogen or $C_{1-20}$ alkyl.

Compositions provided by the present disclosure can comprise from 0.01 wt % to 0.2 wt % such as from 0.03 wt % to 0.13 wt % of a polyamine or a combination of polyamine, where wt % is based on the total weight of the curable composition.

In general, the use of lower molecular weight polyamine curing agents produces harder, less flexible cured sealants, and the use of higher molecular weight polyamine curing agents produces softer, more flexible cured sealants.

Polyamines suitable for use in compositions provided by the present disclosure can be liquid at room temperature. It is desirable that polyamines have a low viscosity at room temperature to facilitate the ability of a polyamine to coat or cover low density filler particles.

Low Density Filler

Compositions provided by the present disclosure can include a low density filler.

Compositions provided by the present disclosure can have a specific gravity, for example, from 0.70 to 0.80, from 0.70 to 0.78, from 0.70 to 0.76, from 0.70 to 0.74, or from 0.71 to 0.74.

Compositions and sealants provided by the present disclosure may include one or more light weight, low density fillers. As used herein, low density, when used with reference to such particles means that the particles are characterized by a specific gravity of no more than 0.7, no more than 0.25, or no more than 0.1. Suitable lightweight filler particles often fall within two categories: microspheres and amorphous particles. The specific gravity of microspheres may range from 0.1 to 0.7 and include, for example, polystyrene foam, microspheres of polyacrylates and polyolefins, and silica microspheres having particle sizes ranging from 5 microns to 100 microns and a specific gravity of 0.25 (Eccospheres®). Other examples include alumina/silica microspheres having particle sizes in the range of 5 microns to 300 microns and a specific gravity of 0.7 (Fillite®), aluminum silicate microspheres having a specific gravity of from about 0.45 to about 0.7 (Z-Light®), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of about 40 μm and a density of 0.135 g/cm$^3$ (Henkel). Suitable fillers for decreasing the specific gravity of the composition include, for example, hollow microspheres such as Expancel® microspheres (available from AkzoNobel) or Dualite® low density polymer microspheres (available from Henkel). Compositions provided by the present disclosure include lightweight filler particles comprising an exterior surface coated with a thin coating, such as those described in U.S. Application Publication No. 2010/0041839, which is incorporated by reference in its entirety.

A light weight filler can comprise Expancel® microspheres characterized by a density of 25 kg/m$^3$ or 60 kg/m$^3$, and an average particle diameter from 20 μm to 120 μm. Expancel® microspheres can be provided in expanded form.

A low density filler can comprise less than 2 wt % of a composition, less than 1.5 wt %, less than 1.0 wt %, less than 0.8 wt %, less than 0.75 wt %, less than 0.7 wt %, or less than 0.5 wt % of a composition, where wt % is based on the total dry solids weight of the composition.

A low density filler, also referred to as a light weight filler, refers to microspheres or particles having a density less than 100 kg/m$^3$, less than 80 kg/m$^3$, less than 60 kg/m$^3$, less than 40 kg/m$^3$, or less than 20 kg/m$^3$. For example, a light weight filler can have a density from 10 kg/m$^3$ to 100 kg/m$^3$, from 10 kg/m$^3$ to 80 kg/m$^3$, from 10 kg/m$^3$ to 60 kg/m$^3$, or from 10 kg/m$^3$ to 40 kg/m$^3$. The particles can have an average particle size ranging from, for example, 1 μm to 500 μm, from 5 μm to 300 μm, from 10 μm to 200 μm, or from 20 μm to 100 μm.

A low density filler can comprise microspheres and/or nanospheres.

Compositions can comprise from 5 wt % to 40 wt %, from 5 wt % to 30 wt %, from 5 wt % to 20 wt %, from 5 wt % to 15 wt %, or from 10 wt % to 20 wt % of a low density filler.

The addition of a low density filler to a composition can decrease the weight of the composition by 20% to 50%, such as from 30% to 40%, compared to the weight of the same volume of the composition without the low density filler.

A low density filler can be mixed with the polyamine component to provide polyamine-coated particles. The polyamine-coated low density filler can be combined with an isocyanate-terminated urethane-containing prepolymer to provide a curable composition.

Compositions provided by the present disclosure may also comprise, as the low density filler, polyphenylene sulfide. Polyphenylene sulfide is a thermoplastic engineering resin that exhibits dimensional stability, chemical resistance, and resistance to corrosive and high temperature environments. Polyphenylene sulfide engineering resins are commercially available, for example, under the tradenames Ryton® (Chevron), Techtron® (Quadrant), Fortron® (Celanese), and Torelina® (Toray). Polyphenylene sulfide resins are generally characterized by a density from about 1.3 g/cc to about 1.4 g/cc, or about 1.35 g/cc. Low density polyphenylene sulfide filler, compositions comprising a polyphenylene sulfide filler, and uses thereof are disclosed in U.S. application Ser. No. 14/593,069 filed on Jan. 9, 2015, entitled Low density fuel resistant sulfur-containing polymer compositions and uses thereof, which is incorporated by reference in its entirety.

For use in compositions provided by the present disclosure, a polyphenylene sulfide filler can be characterized by a particle size, for example, from 5 microns to 50 microns, from 5 microns to 75 microns, less than 75 microns, less than 50 microns, or less than 40 microns.

A polyphenylene sulfide filler can be obtained as pellets and then ground to a fine powder and filtered to obtain a desired nominal particle size and/or desired particle size distribution.

Compositions provided by the present disclosure can comprise from about 5 wt % to about 40 wt % of a polyphenylene sulfide filler, from 10 wt % to about 35 wt %, or from about 20 wt % to about 30 wt % of a polyphenylene sulfide filler, where wt % is based on the total weight of the composition when formulated as a coating or sealant.

A low density filler can be combined with a liquid polyamine curing agent and may include less than 10 wt %, less than 7 wt %, or less than 5 wt % of a low boiling solvent such as ethyl acetate and/or butyl acetate to provide a homogenous mixture in which the low density filler particles are covered with the polyamine curing agent. The mixture can be dried to remove the solvent to provide a powder comprising light weight filler particles coated a polyamine curing agent. The polyamine-coated light weight particles or microspheres can be combined with an isocyanate-terminated urethane-containing prepolymer provided by the present disclosure to provide a curable composition.

Formulations

Compositions provided by the present disclosure may comprise one or more additional components suitable for use in aerospace sealants and depend at least in part on the desired performance characteristics of the cured sealant under conditions of use.

Sealants provided by the present disclosure can be suitable for as Class A, Class B, or Class C aerospace sealants. A Class A sealant is typically applied by brushing and has a viscosity from about 150 Poise to 500 Poise. A Class B sealant can be applied by extrusion such as by extrusion suing a pneumatic Semco® gun and is characterized by a high viscosity from about 8,000 Poise to about 16,000 Poise. A Class B sealant can be used for forming fillets and sealing on vertical surfaces where low slump/sag is required. A Class C sealant can be applied using a roller coating or a combed tooth spreader and has a medium viscosity from about 1,000 Poise to about 4,000 Poise. A Class C sealant is used for sealing fay surfaces.

Compositions provided by the present disclosure include curable compositions and cured compositions. A curable composition comprises a mixture of reactants that have not reacted or have partially reacted and where the viscosity of the curable composition is such that the curable composition can still be applied to a part for its intended purpose. The viscosity at which the composition is no longer workable depends in part on the method of application such as whether the composition is applied, for example, by brushing, spraying, roller coating, pressing, or extrusion. A cured composition can refer to a composition in which the components have reacted to an extent as to provide a tack-free surface and to provide a Shore A hardness of at least 30 A.

Compositions provided by the present disclosure may include one or more catalysts. A catalyst can be selected as appropriate for the curing chemistry employed. For example, when curing thiol-terminated antioxidant-containing polythioether prepolymers and polyepoxides, the catalyst can be an amine catalyst. A cure catalyst may be present in an amount from 0.1 to 5 weight percent, based on the total weight of the composition. Examples of suitable catalysts include 1,4-diazabicyclo[2.2.2]octane (DABCO®, Air Products and DMP-30® (an accelerant composition including 2,4,6-tris(dimethylaminomethyl)phenol).

Compositions provided by the present disclosure can comprise one or more than one adhesion promoters. A one or more additional adhesion promoter may be present in amount from 0.1 wt % to 15 wt % of a composition, less than 5 wt %, less than 2 wt %, or, less than 1 wt %, based on the total dry weight of the composition. Examples of adhesion promoters include phenolics, such as Methylon® phenolic resin, and organosilanes, such as epoxy, mercapto or amino functional silanes, such as Silquest® A-187 and Silquest® A-1100. Other useful adhesion promoters are known in the art.

Suitable adhesion promoters include sulfur-containing adhesion promoters such as those disclosed in U.S. Pat. No. 8,513,339, which is incorporated by reference.

Compositions provided by the present disclosure may comprise one or more different types of filler. Suitable fillers include those commonly known in the art, including inorganic fillers, such as carbon black and calcium carbonate (CaCO$_3$), silica, polymer powders, and lightweight fillers. Suitable lightweight fillers include, for example, those described in U.S. Pat. No. 6,525,168. A composition can include 5 wt % to 60 wt % of the filler or combination of fillers, 10 wt % to 50 wt %, or from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst. Examples of electrically non-conductive fillers include materials such as, but not limited to, calcium carbonate, mica, polyamide, fumed silica, molecular sieve powder, microspheres, titanium dioxide, chalks, alkaline blacks, cellulose, zinc sulfide, heavy spar, alkaline earth oxides, alkaline earth hydroxides, and the like.

Compositions provided by the present disclosure can comprise an electrically conductive filler. Electrical conductivity and EMI/RFI shielding effectiveness can be imparted to composition by incorporating conductive materials within the polymer. The conductive elements can include, for example, metal or metal-plated particles, fabrics, meshes, fibers, and combinations thereof. The metal can be in the form of, for example, filaments, particles, flakes, or spheres. Examples of metals include copper, nickel, silver, aluminum, tin, and steel. Other conductive materials that can be used to impart electrical conductivity and EMI/RFI shielding effectiveness to polymer compositions include conductive particles or fibers comprising carbon or graphite. Conductive polymers such as polythiophenes, polypyrroles, polyaniline, poly(p-phenylene) vinylene, polyphenylene sulfide, polyphenylene, and polyacetylene can also be used. Electrically conductive fillers also include high band gap materials such as zinc sulfide and inorganic barium compounds.

Other examples of electrically conductive fillers include electrically conductive noble metal-based fillers such as pure silver; noble metal-plated noble metals such as silver-plated gold; noble metal-plated non-noble metals such as silver plated cooper, nickel or aluminum, for example, silver-plated aluminum core particles or platinum-plated copper particles; noble-metal plated glass, plastic or ceramics such as silver-plated glass microspheres, noble-metal plated aluminum or noble-metal plated plastic microspheres; noble-metal plated mica; and other such noble-metal conductive fillers. Non-noble metal-based materials can also be used and include, for example, non-noble metal-plated non-noble metals such as copper-coated iron particles or nickel plated copper; non-noble metals, e.g., copper, aluminum, nickel, cobalt; non-noble-metal-plated-non-metals, e.g., nickel-plated graphite and non-metal materials such as carbon black and graphite. Combinations of electrically conductive fillers can also be used to meet the desired conductivity, EMI/RFI shielding effectiveness, hardness, and other properties suitable for a particular application.

An electrically conductive filler can comprise a metal coated fabric such as metal-coated polyester, nylon, spandex, polyolefin, and/or aramids. The metal coating can include a metal such as silver or a combination of metals such as silver/copper, silver/copper/nickel, or silver/copper/tin.

The shape and size of the electrically conductive fillers used in the compositions of the present disclosure can be any appropriate shape and size to impart electrical conductivity and EMI/RFI shielding effectiveness to the cured composition. For example, fillers can be of any shape generally used in the manufacture of electrically conductive fillers, including spherical, flake, platelet, particle, powder, irregular, fiber, and the like. In certain sealant compositions of the disclosure, a base composition can comprise Ni-coated graphite as a particle, powder or flake. The amount of Ni-coated graphite in a base composition can range from 40 wt % to 80 wt %, or can range from 50 wt % to 70 wt %, based on the total weight of the base composition. An electrically conductive filler can comprise Ni fiber. Ni fiber can have a diameter ranging from 10 µm to 50 µm and have a length ranging from 250 µm to 750 µm. A base composition can comprise, for example, an amount of Ni fiber ranging from 2 wt % to 10 wt %, or from 4 wt % to 8 wt %, based on the total weight of the base composition.

Carbon fibers, particularly graphitized carbon fibers, can also be used to impart electrical conductivity to compositions of the present disclosure. Carbon fibers formed by vapor phase pyrolysis methods and graphitized by heat treatment and which are hollow or solid with a fiber diameter ranging from 0.1 micron to several microns, have high electrical conductivity. As disclosed in U.S. Pat. No. 6,184,280, carbon microfibers, nanotubes or carbon fibrils having an outer diameter of less than 0.1 µm to tens of nanometers can be used as electrically conductive fillers. An example of graphitized carbon fiber suitable for conductive compositions of the present disclosure include Panex® 3OMF (Zoltek Companies, Inc., St. Louis, Mo.), a 0.921 µm diameter round fiber having an electrical resistivity of 0.00055 Ω-cm.

The average particle size of an electrically conductive filler can be within a range useful for imparting electrical conductivity to a polymer-based composition. For example, the particle size of the one or more fillers can range from 0.25 µm to 250 µm, or can range from 0.25 µm to 75 µm, or can range from 0.25 µm to 60 µm. A composition of the present disclosure can comprise Ketjenblack® EC-600 JD (Akzo Nobel, Inc., Chicago, Ill.), an electrically conductive carbon black characterized by an iodine absorption of 1,000 mg/g to 11,500 mg/g (J0/84-5 test method), and a pore volume of 480 $cm^3$/100 g to 510 $cm^3$/100 g (DBP absorption, KTM 81-3504). An electrically conductive carbon black filler is Black Pearls® 2000 (Cabot Corporation, Boston, Mass.).

Electrically conductive polymers can be used to impart electrical conductivity or modify the electrical conductivity of compositions of the present disclosure. Polymers having sulfur atoms incorporated into aromatic groups or adjacent to double bonds, such as in polyphenylene sulfide, and polythiophene, are known to be electrically conductive. Other electrically conductive polymers include, for example, polypyrroles, polyaniline, poly(p-phenylene) vinylene, and polyacetylene. A sulfur-containing prepolymer forming a base composition can be polysulfides and/or polythioethers. As such, the sulfur-containing prepolymers can comprise aromatic sulfur groups and sulfur atoms adjacent to conjugated double bonds to enhance the electrical conductivity of the compositions of the present disclosure.

Compositions of the present disclosure can comprise more than one electrically conductive filler and the more than one electrically conductive filler can be of the same or different materials and/or shapes. For example, a sealant composition can comprise electrically conductive Ni fibers, and electrically conductive Ni-coated graphite in the form of powder, particles or flakes. The amount and type of electrically conductive filler can be selected to produce a sealant composition which, when cured, exhibits a sheet resistance (four-point resistance) of less than 0.50 Ω/$cm^2$, or a sheet resistance less than 0.15 Ω/$cm^2$. The amount and type of filler can also be selected to provide effective EMI/RFI shielding over a frequency range of from 1 MHz to 18 GHz for an aperture sealed using a sealant composition of the present disclosure.

An electrically conductive base composition can comprise an amount of electrically non-conductive filler ranging from 2 wt % to 10 wt % based on the total weight of the base composition, or can range from 3 wt % to 7 wt %. A curing agent composition can comprise an amount of electrically non-conductive filler ranging from less than 6 wt % or ranging from 0.5% to 4% by weight, based on the total weight of the curing agent composition.

Galvanic corrosion of dissimilar metal surfaces and the conductive compositions of the present disclosure can be minimized or prevented by adding corrosion inhibitors to the composition, and/or by selecting appropriate conductive fillers. Corrosion inhibitors include strontium chromate, calcium chromate, magnesium chromate, and combinations thereof. U.S. Pat. No. 5,284,888 and U.S. Pat. No. 5,270,364 disclose the use of aromatic triazoles to inhibit corrosion of aluminum and steel surfaces. A sacrificial oxygen scavenger such as Zn can be used as a corrosion inhibitor. A corrosion inhibitor can comprise less than 10% by weight of the total weight of the electrically conductive composition. A corrosion inhibitor can comprise an amount ranging from 2 wt % to 8 wt % of the total weight of the electrically conductive composition. Corrosion between dissimilar metal surfaces can also be minimized or prevented by the selection of the type, amount, and properties of the conductive fillers comprising the composition.

A composition may also include any number of additives as desired. Examples of suitable additives include plasticizers, pigments, surfactants, adhesion promoters, thixotropic agents, fire retardants, masking agents, and accelerators, and combinations of any of the foregoing. When used, the additives may be present in a composition in an amount ranging, for example, from about 0.5% to 60% by weight, where wt % is based on the total solids weight of the composition. Additives may be present in a composition in an amount ranging from about 25 wt % to 60 wt %.

Uses

Compositions provided by the present disclosure may be used, for example, in sealants, coatings, encapsulants, and potting compositions. A sealant includes a composition capable of producing a film that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. Sealant compositions provided by the present disclosure are useful, e.g., as aerospace sealants and as linings for fuel tanks.

Compositions, such as sealants, may be provided as multi-pack compositions, such as two-pack compositions, wherein one package comprises one or more reactive antioxidants and/or antioxidant-containing prepolymers provided by the present disclosure and a second package comprises one or more polyfunctional sulfur-containing epoxies provided by the present disclosure. Additives and/or other materials may be added to either package as desired or necessary. The two packages may be combined and mixed prior to use. The pot life of the one or more mixed reactive antioxidants and/or antioxidant-containing prepolymers and epoxies is at least 30 minutes, at least 1 hour, at least 2 hours, or more than 2 hours, where pot life refers to the period of time the mixed composition remains suitable for use as a sealant after mixing.

Compositions, including sealants, provided by the present disclosure may be applied to any of a variety of substrates. Examples of substrates to which a composition may be applied include metals such as titanium, stainless steel, aluminum, and alloys thereof, any of which may be anodized, primed, organic-coated or chromate-coated; epoxy; urethane; graphite; fiberglass composite; Kevlar®; acrylics; and polycarbonates. Compositions provided by the present disclosure may be applied to a coating on a substrate, such as a polyurethane coating. Compositions comprising antioxidant-containing polythioethers or antioxidant-containing prepolymers provided by the present disclosure exhibit enhanced adhesion to aluminum, aluminum oxide, anodized aluminum, titanium, titanium oxide, and/or Alodine® surfaces, compared to similar compositions without an antioxidant.

Compositions provided by the present disclosure may be applied directly onto the surface of a substrate or over an underlayer by any suitable coating process known to those of ordinary skill in the art.

Furthermore, methods are provided for sealing a part using a composition provided by the present disclosure. These methods comprise, for example, applying a composition provided by the present disclosure to a surface of a part, and curing the composition. For example, methods of sealing a part, comprise preparing a curable composition comprising the a reactive antioxidant or antioxidant-containing prepolymer provided by the present disclosure, applying the curable composition to a part; and curing the curable composition to seal the part.

Parts sealed with a sealant composition of the present disclosure are provided.

Properties

For aerospace sealant applications it is desirable that a sealant meet the requirements of Mil-S-22473E (Sealant Class C) at a cured thickness of 20 mils, exhibit an elongation greater than 200%, a tensile strength greater than 250 psi, and excellent fuel resistance, and maintain these properties over a wide temperature range from −67° F. to 360° F. In general, the visual appearance of the sealant is not an important attribute. Prior to full cure, a sealant provided by the present disclosure can have a working time of at least 12 hours, at least 16 hours, or at least 20 hours at room temperature. After the sealant is partially cured and is no longer workable sealants provided by the present disclosure can have a tack-free cure time of less than 4 hours, less than 8 hours, less than 12 hours, or less than 24 hours. Working time refers to the time period the sealant remains workable or spreadable for application at ambient temperatures after the composition has been heated to activate the blocked DBU catalyst. For example, a numerical scale can be used to assess the working time where (1) represents the workability of the initially activated sealant; (2) represents a sealant having a viscosity slightly greater than the initially activated sealant; (3) represents a sealant having a significantly greater viscosity than that of the initially activated sealant; (4) represents a sealant that has begun to gel but remains spreadable; (5) represents a sealant that has gelled but is no longer spreadable; (6) represents a sealant that has almost cured, but is not tack-free; (7) represents a sealant that is cured to a tack-free condition; (8) represents a cured sealant having Shore A hardness of 20 A; (9) represents a cured sealant having Shore A hardness of 35 A; and (10) represents a cured sealant having Shore A hardness of 45 A.

A composition may be cured under ambient conditions, where ambient conditions refers to a temperature from 20° C. to 25° C., and atmospheric humidity. A composition may be cured under conditions encompassing a temperature from a 0° C. to 100° C. and humidity from 0% relative humidity to 100% relative humidity. A composition may be cured at a higher temperature such as at least 30° C., at least 40° C., or at least 50° C. A composition may be cured at room temperature, e.g., 25° C. A composition may be cured upon exposure to actinic radiation, such as ultraviolet radiation. As will also be appreciated, the methods may be used to seal apertures on aerospace vehicles including aircraft and aerospace vehicles.

A composition can achieve a tack-free cure in less than about 2 hours, less than about 4 hours, less than about 6 hours, less than about 8 hours, or in less than about 10 hours, at a temperature of less than about 200° F.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within 24 hours to 30 hours, and 90% of full adhesion strength develops from 2 days to 3 days, following mixing and application to a surface. In general, full adhesion strength as well as other properties of cured compositions of the present disclosure becomes fully developed within 7 days following mixing and application of a curable composition to a surface.

Cured compositions disclosed herein, such as cured sealants, exhibit properties acceptable for use in aerospace applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in Jet Reference Fluid (JRF) Type I for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aviation and aerospace applications are disclosed in AMS 3265B, which is incorporated by reference in its entirety. It is also desirable that, when cured, compositions of the present disclosure used in aviation and aircraft applications exhibit a percent volume swell not greater than 25% following immersion for one week at 60° C. (140° F.) and ambient pressure in JRF Type I. Other properties, ranges, and/or thresholds may be appropriate for other sealant applications.

Compositions provided by the present disclosure are fuel-resistant. As used herein, the term "fuel resistant" means that a composition, when applied to a substrate and cured, can provide a cured product, such as a sealant, that exhibits a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification). Jet Reference Fluid JRF Type I, as employed for determination of fuel resistance, has the following composition: toluene: 28%±1% by volume; cyclohexane (technical): 34%±1% by volume; isooctane: 38%±1% by volume; and tertiary dibutyl disulfide: 1%±0.005% by volume (see AMS 2629, issued Jul. 1, 1989, § 3.1.1, etc., available from SAE (Society of Automotive Engineers)).

Compositions provided herein provide a cured product, such as a sealant, exhibiting a elongation of at least 100% and a tensile strength of at least 400 psi when measured in accordance with the procedure described in AMS 3279, § 3.3.17.1, test procedure AS5127/1, § 7.7.

Compositions provide a cured product, such as a sealant, that exhibits a lap shear strength of greater than 200 psi, such as at least 220 psi, at least 250 psi, and, in some cases, at least 400 psi, when measured according to the procedure described in SAE AS5127/1 paragraph 7.8.

A cured sealant comprising a composition provided by the present disclosure meets or exceeds the requirements for aerospace sealants as set forth in AMS 3277.

Apertures, including apertures of aerospace vehicles, sealed with compositions provided by the present disclosure are also disclosed.

A cured sealant provided by the present disclosure exhibits the following properties when cured for 2 days at room temperature, 1 day at 140° F. and 1 day at 200° F.: a dry hardness of 49, a tensile strength of 428 psi, and an elongation of 266%; and after 7 days in JRF Type I, a hardness of 36, a tensile strength of 312 psi, and an elongation of 247%.

Compositions provided by the present disclosure exhibit a Shore A hardness (7-day cure) greater than 10, greater than 20, greater than 30, or greater than 40; a tensile strength greater than 10 psi, greater than 100 psi, greater than 200 psi, or greater than 500 psi; an elongation greater than 100%, greater than 200%, greater than 500%, or greater than 1,000%; and a swell following exposure to JRF Type I (7 days) less than 20%.

EXAMPLES

The present invention is further illustrated by reference to the following examples, which describe the synthesis, properties, and uses of certain polythiol adducts, prepolymers formed using the polythiol adducts, compositions comprising the prepolymers and cured sealants prepared using compositions. It will be apparent to those skilled in the art that many modifications, both to materials, and methods, may be practiced without departing from the scope of the disclosure.

Example 1

Synthesis of Polythiol Adducts 1,5-Dimercapto-3-thiapentane (DMDS) and methyl ethyl ketone (MEK) were reacted in a 2:1 molar ratio in the presence of para-toluene sulfonic acid (p-TsOH) and cyclohexane as a co-solvent at a temperature from 90° C. to 95° C. to provide a polythiol adduct. The reaction was continued until the ketone infrared peak at 1713 cm$^{-1}$ was no longer present. The polythiol adduct was present as a water-clear liquid.

Alternatively DMDS and MEK were reacted in a 3:2 molar ratio to provide an extended polythiol adduct.

A thiol-terminated urethane-extended adduct was obtained by reacting the polythiol adduct with Desmodur® W (H$_{12}$MDI diisocyanate) in a 2:1 ratio in the presence of dibutyl tin dilaurate (DBTL) catalyst at a temperature from 75° C. to 95° C. for 27 h. The product was solid at room temperature.

Example 2

Synthesis of Isocyanate-Terminated Urethane-Containing Prepolymers

A thiol-terminated polysulfide prepolymer (Thioplast® G-112 or Thiokol® L-32), the polythiol adduct of Example 1, and a diisocyanate (H$_{12}$MDI) were combined and heated to a temperature of 70° C. in the presence of a Polycat® 8 catalyst to provide an isocyanate-terminated urethane-containing prepolymer. The equivalent ratio of the thiol-terminated polysulfide prepolymer to polythiol adduct was from 2:5 to 1.5:4, such as 1:3. The ratio of diisocyanate equivalents to thiol equivalents was from 5:1 to 2:1.

Example 3

Synthesis of Isocyanate-Terminated Urethane-Containing Prepolymers

In two-step method of preparing an isocyanate-terminated urethane-containing prepolymer, a diisocyanate (H$_{12}$MDI) and a thiol-terminated polysulfide prepolymer (Thioplast® G-112 or Thiokol® L-32) were combined and heated to a temperature of 70° C. to 75° C. in the presence of Polycat® 8 catalyst (N,N'-dimethylcyclohexylamine) to provide an isocyanate-terminated polysulfide prepolymer.

In a second step, the polythiol adduct of Example 1 was combined with the isocyanate-terminated polysulfide prepolymer in the first step and a diisocyanate, and the mixture reacted at a temperature of 70° C. to 75° C. in the presence of Polycat® 8 catalyst to provide an isocyanate-terminated urethane-containing prepolymer.

The ratio of isocyanate equivalents to thiol equivalents was from 5:1 to 2:1.

Example 4

Low Density Sealant Compositions

To prepare a low density sealant composition, Expancel® microspheres were combined with a liquid polyamine, (Jefflink® 754), in the presence of less than 10 wt % of ethyl acetate and/or butyl acetate to provide a homogeneous mixture of polyamine-coated low density microspheres. The mixture was dried in an oven to produce a dry powder.

The polyamine-coated low density microspheres were then combined with the isocyanate-terminated urethane-containing prepolymer of Example 2 or Example 3 and a low boiling point solvent.

The curable composition was poured into a Teflon® mold and cured for 16 hours at room temperature. The cured sealant exhibited a Shore A hardness of 50 and a Shore D hardness of 12. The cured film had a density of 0.73 g/L. The cured sealant passed the NaCl immersion resistance and aviation fluid resistance tests according to AS 5127/1C.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A urethane-extended polythiol adduct comprising the reaction product of reactants comprising:
a polythiol adduct wherein the polythiol adduct comprises the condensation reaction products of reactants comprising a polythiol and a ketone; and
a diisocyanate.

2. A urethane-extended polythiol adduct having the structure of Formula (7):

HS—[-A-S—C(═O)—NH—R$^5$—NH—C(═O)—S—]$_m$-A-SH　　(7)

wherein,
each R$^5$ independently comprises a core of a diisocyanate;
m is an integer from 1 to 10;
each A independently comprises a moiety having the structure of Formula (6a):

-(—R$^1$—S—R$^2$—S—)$_n$—R$^1$—　　(6a)

wherein,
n is an integer from 1 to 10;
each R$^1$ independently comprises a structure of Formula (1a):

-[—(CHR$^3$)$_p$—X—]$_q$—(CHR$^3$)$_r$—　　(1a)

wherein,
each R$^3$ comprises hydrogen or methyl;
each X is independently selected from O and S;
p is an integer from 2 to 6;
q is an integer from 1 to 5; and
r is an integer from 2 to 10; and
each R$^2$ independently comprises a moiety having the structure of Formula (3a):

—C(—R$^4$)$_2$—　　(3a)

wherein each R$^4$ independently comprises C$_{1-5}$ alkyl.

3. An isocyanate-terminated urethane-containing prepolymer comprising the reaction product of reactants comprising:
a polythiol adduct, wherein the polythiol adduct comprises the condensation reaction products of reactants comprising: a polythiol; and a ketone of claim 1;
a thiol-terminated sulfur-containing prepolymer; and
a diisocyanate.

4. The isocyanate-terminated urethane-containing prepolymer of claim 3, wherein,
the diisocyanate comprises an aliphatic diisocyanate, an aromatic diisocyanate, or a combination thereof; and
the thiol-terminated sulfur-containing prepolymer comprises a thiol-terminated polythioether, a thiol-terminated polysulfide, or a combination thereof.

5. The isocyanate-terminated urethane-containing prepolymer of claim 3, wherein the thiol-terminated sulfur-containing prepolymer comprises a thiol-terminated sulfur-containing prepolymer of Formula (9a), a thiol-terminated sulfur-containing prepolymer of Formula (9b), a thiol-terminated sulfur-containing prepolymer of Formula (9c), or a combination of any of the foregoing:

HS—P—SH　　(9a)

{HS—P—S—V'—}$_z$B　　(9b)

{HS—(—R$^6$—S—S—)$_a$—CH$_2$—}$_2$CH—(—S—S—R$^6$—)$_a$—SH　　(9c)

wherein,
each P independently comprises a polythioether moiety or a polysulfide moiety;
B represents a core of a z-valent, polyfunctionalizing agent B(—V)$_z$ wherein,
z is an integer from 3 to 6; and
each V is a moiety comprising a terminal group reactive with a thiol;
each —V'— is derived from the reaction of —V with a thiol;
each a is independently an integer from 1 to 50;
the sum of each a is an integer from 3 to 60; and
each R$^6$ comprises a moiety having the structure —(CH$_2$)$_2$—O—CH$_2$—O—(CH$_2$)$_2$—.

6. The isocyanate-terminated urethane-containing prepolymer of claim 3, wherein the polythiol adduct comprises:
(a) a moiety of Formula (6a):

-(—R$^1$—S—R$^2$—S—)$_n$—R$^1$—　　(6a)

wherein,
n is an integer from 1 to 10;
each R$^1$ independently comprises a structure of Formula (1a):

-[—(CHR$^3$)$_p$—X—]$_q$—(CHR$^3$)$_r$—　　(1a)

wherein,
each R$^3$ comprises hydrogen or methyl;
each X is independently selected from O and S;
p is an integer from 2 to 6;
q is an integer from 1 to 5; and
r is an integer from 2 to 10; and
each R$^2$ independently comprises a moiety having the structure of Formula (3a):

—C(—R$^4$)$_2$—　　(3a)

wherein each R$^4$ independently comprises C$_{1-5}$ alkyl;
(b) a moiety of Formula (7a):

-[-A-S—C(═O)—NH—R$^5$—NH—C(═O)—S—]$_m$-A-　　(7a)

wherein,
each R$^5$ independently comprises a core of a diisocyanate;
m is an integer from 1 to 10; and
each A independently comprises a moiety having the structure of Formula (6a):

-(—R$^1$—S—R$^2$—S—)$_n$—R$^1$—　　(6a)

wherein,
n is an integer from 1 to 10;
each R$^1$ independently comprises a structure of Formula (1a):

-[—(CHR$^3$)$_p$—X—]$_q$—(CHR$^3$)$_r$—　　(1a)

wherein,
each R$^3$ comprises hydrogen or methyl;
each X is independently selected from O and S;
p is an integer from 2 to 6;
q is an integer from 1 to 5; and
r is an integer from 2 to 10; and
each R$^2$ independently comprises a moiety having the structure of Formula (3a):

—C(—R$^4$)$_2$—　　(3a)

wherein each R$^4$ independently comprises C$_{1-5}$ alkyl; or
(c) a combination thereof.

7. The isocyanate-terminated urethane-containing prepolymer of claim 3, wherein the thiol-terminated sulfur-containing prepolymer comprises a thiol-terminated polythioether prepolymer of Formula (11a), a thiol-terminated polythioether prepolymer of Formula (11b), or a combination thereof:

$$HS-R^1-[-S-(CH_2)_2-O-(R^2-O)_m-(CH_2)_2-S-R^1-]_n-SH \quad (11a)$$

$$\{HS-R^1-[-S-(CH_2)_2-O-(R^2-O)_m-(CH_2)_2-S-R^1-]_n-S-V'-\}_z B \quad (11b)$$

wherein,
each $R^1$ independently is selected from $C_{2-10}$ alkanediyl, $C_{6-8}$ cycloalkanediyl, $C_{6-14}$ alkanecycloalkanediyl, $C_{5-8}$ heterocycloalkanediyl, and $-[(-CHR^3-)_p-X-]_q-(-CHR^3-)_r-$, wherein,
p is an integer from 2 to 6;
q is an integer from 1 to 5;
r is an integer from 2 to 10;
each $R^3$ is independently selected from hydrogen and methyl; and
each X is independently selected from $-O-$, $-S-$, $-NH-$, and $-N(-CH_3)-$;
each $R^2$ is independently selected from $C_{1-10}$ alkanediyl, $C_{6-8}$ cycloalkanediyl, $C_{6-14}$ alkanecycloalkanediyl, and $-[(-CHR^3-)_p-X-]_q-(-CHR^3-)_r-$, wherein p, q, r, $R^3$, and X are as defined as for R';
m is an integer from 0 to 50;
n is an integer from 1 to 60;
B represents a core of a z-valent, polyfunctionalizing agent $B(-V)_z$ wherein,
z is an integer from 3 to 6; and
each V is a moiety comprising a terminal group reactive with a thiol; and
each $-V'-$ is derived from the reaction of $-V$ with a thiol.

8. The isocyanate-terminated urethane-containing prepolymer of claim 3, wherein the thiol-terminated sulfur-containing prepolymer comprises a thiol-terminated polysulfide prepolymer having the structure of Formula (9c):

$$\{HS-(-R^6-S-S-)_a-CH_2-\}_2CH-(-S-S-R^6-)_a-SH \quad (9c)$$

wherein,
each a is independently an integer from 1 to 50;
the sum of each a is an integer from 3 to 60; and
each $R^6$ comprises a moiety having the structure $-(CH_2)_2-O-CH_2-O-(CH_2)_2-$.

9. An isocyanate-terminated urethane-containing prepolymer comprising the reaction products of reactants comprising:
an isocyanate-terminated sulfur-containing prepolymer, a polythiol adduct, and a diisocyanate; wherein,
the isocyanate-terminated prepolymer comprises the reaction product of reactants comprising a diisocyanate and a thiol-terminated sulfur-containing prepolymer; and
the polythiol adduct comprises the condensation reaction products of reactants comprising a polythiol and a ketone.

10. An isocyanate-terminated urethane-containing prepolymer comprising an isocyanate-terminated urethane-containing prepolymer of Formula (15a), an isocyanate-terminated urethane-containing prepolymer of Formula (15b), or a combination thereof:

$$D-S-P-S-D \quad (15a)$$

$$\{D-S-P-S-V'-\}_z B \quad (15b)$$

wherein,
each D independently comprises a moiety having the structure of Formula (16a), Formula (16b), Formula (16c), Formula (16d), Formula (16e), Formula (16f), Formula (16g), or a combination of any of the foregoing:

$$-C(=O)-NH-R^5-N=C=O \quad (16a)$$

$$-C(=O)-NH-R^5-[-NH-C(=O)-S-E-S-C(=O)-NH-R^5-]_m-N=C=O \quad (16b)$$

$$-C(=O)-NH-R^5-[-NH-C(=O)-S-E-S-C(=O)-NH-R^5-]_m-NH-C(=O)-S-P-S-V'-B\{-V'-S-P-S-C(=O)-NH-R^5-N=C=O\}_{z-1} \quad (16c)$$

$$-C(=O)-NH-R^5-\{-NH-C(=O)-S-E-S-C(=O)-NH-R^5-\}_m-NH-C(=O)-S-P-S-V'-B\{-V'-S-P-S-C(=O)-NH-R^5-[-NH-C(=O)-S-E-S-C(=O)-NH-R^5-]_m-N=C=O\}_{z-1} \quad (16d)$$

$$-C(=O)-NH-R^5-NH-C(=O)-S-P-S-V'-B\{-V'-S-P-S-C(=O)-NH-R^5-N=C=O\}_{z-1} \quad (16e)$$

$$-C(=O)-NH-R^5-NH-C(=O)-S-P-S-V'-B\{-V'-S-P-S-C(=O)-NH-R^5-[-NH-C(=O)-S-E-S-C(=O)-NH-R^5-]_m-N=C=O\}_{z-1} \quad (16f)$$

$$-C(=O)-NH-R^5-[-NH-C(=O)-S-E-S-C(=O)-NH-R^5-]_m-NH-C(=O)-S-P-S-V'-B\{-V'-S-P-S-C(=O)-NH-R^5-[-NH-C(=O)-S-E-S-C(=O)-NH-R^5-]_m-N=C=O\}_{z-1} \quad (16g)$$

wherein,
each $R^5$ independently comprises a core of a diisocyanate;
each m is an integer from 1 to 10;
each P comprises a polythioether moiety or a polysulfide moiety;
B represents a core of a z-valent, polyfunctionalizing agent $B(-V)_z$ wherein,
z is an integer from 3 to 6; and
each V is a moiety comprising a terminal group reactive with a thiol; and
each $-V'-$ is derived from the reaction of $-V$ with a thiol,
wherein
(a) each E independently comprises a core of a polythiol adduct wherein the polythiol adduct comprises the condensation reaction products of reactants comprising a polythiol and a ketone; having the structure of Formula (6a):

$$-(-R^1-S-R^2-S-)_n-R^1- \quad (6a)$$

wherein
n is an integer from 1 to 10;
each $R^1$ independently comprises a structure of Formula (1a):

$$-[-(CHR^3)_p-X-]_q-(CHR^3)_r- \quad (1a)$$

wherein
each $R^3$ comprises hydrogen or methyl;
each X is independently selected from O and S;
p is an integer from 2 to 6;
q is an integer from 1 to 5; and
r is an integer from 2 to 10;

each $R^2$ independently comprises a moiety having the structure of Formula (3a):

$$—C(—R^4)_2— \quad (3a)$$

wherein each $R^4$ independently comprises $C_{1-5}$ alkyl; or (b) each E independently comprises a core of a urethane-containing polythiol adduct having the structure of Formula (7a):

$$-(-A-S—C(=O)—NH—R^5—NH—C(=O)—S—)_m-A- \quad (7a)$$

wherein,
each $R^5$ independently comprises a core of a diisocyanate;
m is an integer from 1 to 10; and
each A independently comprises a moiety having the structure of Formula (6a).

11. The isocyanate-terminated urethane-containing prepolymer of claim 10, wherein each P independently comprises a moiety of Formula (11c):

$$—R^1—[—S—(CH_2)_2—O—(R^2—O)_m—(CH_2)_2—S—R^1—]_n- \quad (11c)$$

12. An isocyanate-terminated urethane-containing prepolymer comprising an isocyanate-terminated urethane-containing prepolymer of Formula (19):

$$\{D-S-\}_3G \quad (19)$$

wherein,
G is a moiety of Formula (9d):

$$\{-(—R^6—S—S—)_a—CH_2—\}_2CH—(—S—S—R^6—)_a- \quad (9d)$$

wherein,
each a is independently an integer from 1 to 50;
the sum of each a is an integer from 5 to 60; and
each $R^6$ comprises a moiety having the structure $—(CH_2)_2—O—CH_2—O—(CH_2)_2—$; and
each D independently comprises a moiety having the structure of Formula (20a), Formula (20b), Formula (20c) or Formula (20d):

$$—C(=O)—NH—R^5—N=C=O \quad (20a)$$

$$—C(=O)—NH—R^5—[—NH—C(=O)—S-E-S—C(=O)—NH—R^5—]_m—N=C=O \quad (20b)$$

$$—C(=O)—NH—R^5—NH—C(=O)—S-G\{-S-D'\}_2 \quad (20c)$$

$$—C(=O)—NH—R^5—[—NH—C(=O)—S-E-S—C(=O)—NH—R^5—]_m—NH—C(=O)—S-G\{-S-D'\}_2 \quad (20d)$$

wherein,
each $R^5$ independently comprises a core of a diisocyanate; and
each m is an integer from 1 to 10; and
each E comprises a core of a polythiol adduct or a core of a urethane-containing polythiol adduct wherein the polythiol adduct comprises the condensation reaction products of reactants comprising a polythiol and a ketone; and
each D' comprises a moiety of Formula (20a) or a moiety of Formula (20b).

13. A composition comprising the isocyanate-terminated urethane-containing prepolymer of claim 3.

14. The composition of claim 13, wherein the composition comprises a low density filler.

15. The composition of claim 13, formulated as a sealant.

16. A part comprising a sealant prepared from the composition of claim 13.

17. A method of sealing a part, wherein the method comprises:
providing a curable composition comprising the composition of claim 13;
applying the curable composition to at least a portion of a surface of a part; and
curing the applied curable composition to seal the part.

18. The part of claim 16, wherein the part comprises a part of an aerospace vehicle.

19. The method of claim 17, wherein the part comprises a part of an aerospace vehicle.

20. A composition comprising the isocyanate-terminated urethane-containing prepolymer of claim 9.

21. A part comprising a sealant prepared from the composition of claim 20.

22. The part of claim 21, wherein the part comprises a part of an aerospace vehicle.

23. A method of sealing a part, wherein the method comprises:
providing a curable composition comprising the composition of claim 20;
applying the curable composition to at least a portion of a surface of a part; and
curing the applied curable composition to seal the part.

24. The method of claim 23, wherein the part comprises a part of an aerospace vehicle.

25. A composition comprising the isocyanate-terminated urethane-containing prepolymer of claim 10.

26. A part comprising a sealant prepared from the composition of claim 25.

27. The part of claim 26, wherein the part comprises a part of an aerospace vehicle.

28. A method of sealing a part, wherein the method comprises:
providing a curable composition comprising the composition of claim 25;
applying the curable composition to at least a portion of a surface of a part; and
curing the applied curable composition to seal the part.

29. The method of claim 28, wherein the part comprises a part of an aerospace vehicle.

30. A composition comprising the isocyanate-terminated urethane-containing prepolymer of claim 12.

31. A part comprising a sealant prepared from the composition of claim 30.

32. The part of claim 31, wherein the part comprises a part of an aerospace vehicle.

33. A method of sealing a part, wherein the method comprises:
providing a curable composition comprising the composition of claim 30;
applying the curable composition to at least a portion of a surface of a part; and
curing the applied curable composition to seal the part.

34. The method of claim 33, wherein the part comprises a part of an aerospace vehicle.

35. The isocyanate-terminated urethane-containing prepolymer of claim 6 wherein,
each $R^1$ is $—(CH_2)_2—O—CH_2—O—(CH_2)_2—$;
each $R^2$ is $—C(—CH_3)(—CH_2—CH_3)$; and
each $R^5$ is 4,4'-methylenebis(cyclohexan-1-yl).

36. The isocyanate-terminated urethane-containing prepolymer of claim 10 wherein,
each $R^1$ is $—(CH_2)_2—O—CH_2—O—(CH_2)_2—$;
each $R^2$ is $—C(—CH_3)(—CH_2—CH_3)$; and
each $R^5$ is 4,4'-methylenebis(cyclohexan-1-yl).

* * * * *

UNITED STATES PATENT AND TRADEMARK OFFICE
CERTIFICATE OF CORRECTION

PATENT NO. : 9,902,799 B2  
APPLICATION NO. : 14/937904  
DATED : February 27, 2018  
INVENTOR(S) : Razmik Boghossian et al.

Page 1 of 1

It is certified that error appears in the above-identified patent and that said Letters Patent is hereby corrected as shown below:

In the Claims

Column 39, Line 44, Claim 3:  
Delete "of claim 1"

Column 41, Line 25, Claim 7:  
"CHR3-)$^r$-,"  
Should be:  
--CHR3-)$_r$- --

Signed and Sealed this  
Thirteenth Day of November, 2018

Andrei Iancu  
*Director of the United States Patent and Trademark Office*